US009320819B2

(12) United States Patent
Koyama

(10) Patent No.: US 9,320,819 B2
(45) Date of Patent: Apr. 26, 2016

(54) STERILIZATION APPARATUS AND METHOD

(71) Applicants: CANON MARKETING JAPAN KABUSHIKI KAISHA, Tokyo (JP); ELK CORPORATION, Osaka (JP); KABUSHIKI KAISHA ELQUEST, Chiba (JP)

(72) Inventor: Takashi Koyama, Tokyo (JP)

(73) Assignees: CANON MARKETING JAPAN KABUSHIKI KAISHA, Tokyo (JP); ELK CORPORATION, Osaka (JP); KABUSHIKI KAISHA ELQUEST, Chiba (JP)

( * ) Notice: Subject to any disclaimer, the term of this patent is extended or adjusted under 35 U.S.C. 154(b) by 497 days.

(21) Appl. No.: 13/645,157

(22) Filed: Oct. 4, 2012

(65) Prior Publication Data

US 2013/0094995 A1 Apr. 18, 2013

(30) Foreign Application Priority Data

Oct. 6, 2011 (JP) ................................. 2011-222385
Oct. 31, 2011 (JP) ................................. 2011-239563
Oct. 31, 2011 (JP) ................................. 2011-239564
Jul. 11, 2012 (JP) ................................. 2012-155735

(51) Int. Cl.
*G05B 17/00* (2006.01)
*G05B 1/00* (2006.01)
*A61L 2/00* (2006.01)
*A61L 2/18* (2006.01)
*A61L 2/20* (2006.01)

(52) U.S. Cl.
CPC ................. *A61L 2/186* (2013.01); *A61L 2/208* (2013.01); *A61L 2202/11* (2013.01); *A61L 2202/14* (2013.01)

(58) Field of Classification Search
CPC ............................ A61L 2202/14; A61L 2/186
USPC .................................................. 422/105, 116
See application file for complete search history.

(56) References Cited

U.S. PATENT DOCUMENTS

| 4,660,742 | A | * | 4/1987 | Ozdemir ................... B67D 1/12 222/153.09 |
| 5,346,132 | A | * | 9/1994 | Hahn et al. ........................ 239/71 |
| 2003/0190257 | A1 | | 10/2003 | Halstead et al. |
| 2010/0163573 | A1 | * | 7/2010 | Wegelin et al. .................... 222/1 |

FOREIGN PATENT DOCUMENTS

| DE | 2206881 A1 | 8/1973 |
| JP | 2009-148315 A | 7/2009 |

* cited by examiner

*Primary Examiner* — Kevin Joyner
(74) *Attorney, Agent, or Firm* — Canon USA, Inc. IP Division

(57) ABSTRACT

There is provided a mechanism of preventing a cartridge in which a sterilizing agent is remaining from being taken out from a sterilization apparatus in order to prevent a user from touching the sterilizing agent. There is provided a sterilization apparatus for sterilizing an object by extracting a sterilizing agent from a cartridge containing the sterilizing agent. The apparatus includes locking means for locking the cartridge containing the sterilizing agent and mounted on the sterilization apparatus and extracting means for extracting the sterilizing agent from the cartridge, wherein the locking means is configured to maintain the lock on the cartridge until sterilizing agent has been extracted from the cartridge by the extracting means.

13 Claims, 21 Drawing Sheets

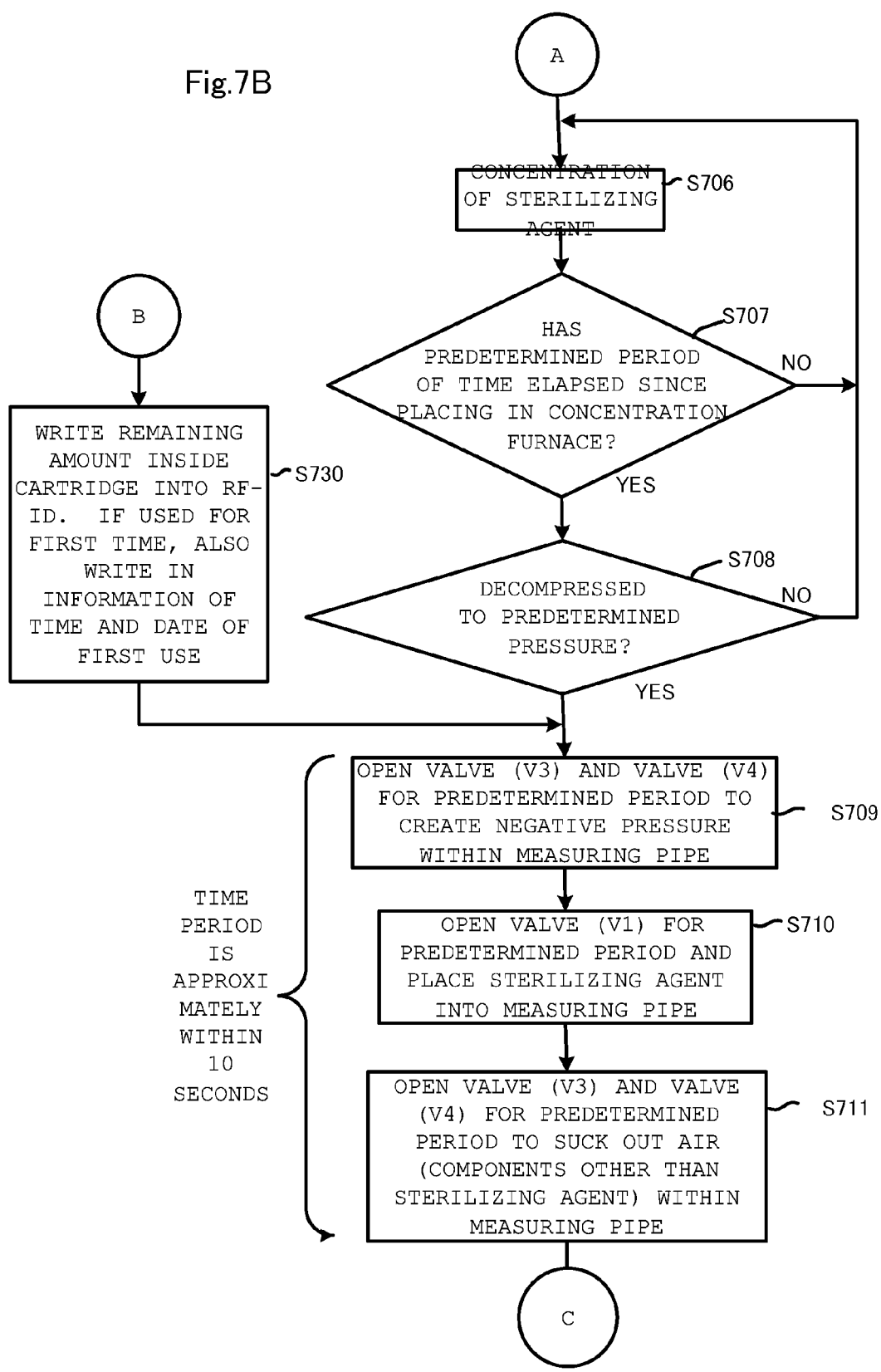

STERILIZATION APPARATUS AND METHOD

BACKGROUND OF THE INVENTION

1. Field of the Invention

The present invention relates to a sterilization apparatus and method. In particular, the present invention relates to a sterilization apparatus and method applicable where a cartridge in which sterilizing agent remains cannot be taken out of the sterilization apparatus.

2. Description of the Related Art

In medical equipment such as syringe needles and surgical tools, there is a concern that pathogens may have been attached thereto after use and this may have an adverse effect on the human body. If the medical equipment is not sterilized after use, it cannot be reused. For this reason, there are sterilization apparatuses which perform a sterilization process on target objects requiring sterilization such as medical equipment.

As one of such sterilization apparatuses, a sterilization apparatus sterilizing an object using hydrogen peroxide as the sterilizing agent, and a sterilization method thereof have been proposed (for example, Japanese Unexamined Patent Application Publication No. 08-505787).

However, there is a problem in a sterilization apparatus for performing a sterilization process on an object by sucking out an amount of sterilizing agent from a cartridge, in which there is an amount of sterilizing agent for performing a sterilization process a plurality of times. In particular, if the user takes out the cartridge with sterilizing agent remaining between a first sterilization process and a second sterilization process being performed, the remaining sterilizing agent may leak to the outside of the sterilization apparatus. If such a leak occurs, the user may unintentionally handle the harmful sterilizing agent (for example, a hydrogen peroxide solution).

Therefore, there is a concern that a user with no knowledge of how to handle the sterilizing agent (for example, a hydrogen peroxide solution) may cause leakage when taking out the sterilizing agent from the sterilization apparatus.

Further, in a case where there is not an amount of sterilizing agent for performing one sterilization process remaining within the cartridge but there is a small amount of sterilizing agent remaining, the sterilizing agent remaining within the cartridge must be disposed of. For example, in a case where the sterilizing agent is a hydrogen peroxide solution, since hydrogen peroxide is a chemical designated as a hazardous substance, there is a disposal cost.

Further, with a sterilizing agent (for example, a hydrogen peroxide solution) inside a cartridge, in a case where the sterilizing agent (for example, a hydrogen peroxide solution) is naturally decomposed after the manufacture of the cartridge and after a certain period of time has elapsed, a sufficient sterilization effect may not be obtained.

Further, in a case where once the use of the sterilizing agent (for example, a hydrogen peroxide solution) inside the cartridge is started, components that promote the decomposition of the hydrogen peroxide may be mixed in or otherwise introduced. If the sterilizing agent is then used after a certain period of time has elapsed since the use of the cartridge has started, a sufficient sterilization effect may not be obtained.

SUMMARY OF THE INVENTION

The present invention is directed to a sterilization apparatus and a sterilization method capable of preventing a cartridge in which there is sterilizing agent remaining from being taken out of the sterilization apparatus so that the user cannot touch the sterilizing agent.

According to an aspect of the present invention there is provided sterilization apparatus as set out in accompanying claims 1 to 15.

According to another aspect of the present invention, a sterilization method is provided as set out in claim 16.

According to yet another aspect of the present invention, a computer program is provided as set out in accompanying claim 17.

Further features and aspects of the present invention will become apparent from the following detailed description of embodiments with reference to the attached drawings.

BRIEF DESCRIPTION OF THE DRAWINGS

The accompanying drawings, which are incorporated in and constitute a part of the specification, illustrate embodiments, features, and aspects of the invention and, together with the description, serve to explain the principles of the invention.

FIGS. 7A, 7B, 7C, and 7D are diagrams illustrating an example of detailed processing of the sterilization step illustrated in step S502 of FIG. 5.

DESCRIPTION OF THE EMBODIMENTS

Various embodiments of the invention are described in detail below with reference to the drawings.

A sterilization apparatus according to a first embodiment of the present invention will now be described below with reference to the drawings. First, the external appearance of the sterilization apparatus according to the present invention will be described by reference to FIG. 1.

Figure 1:
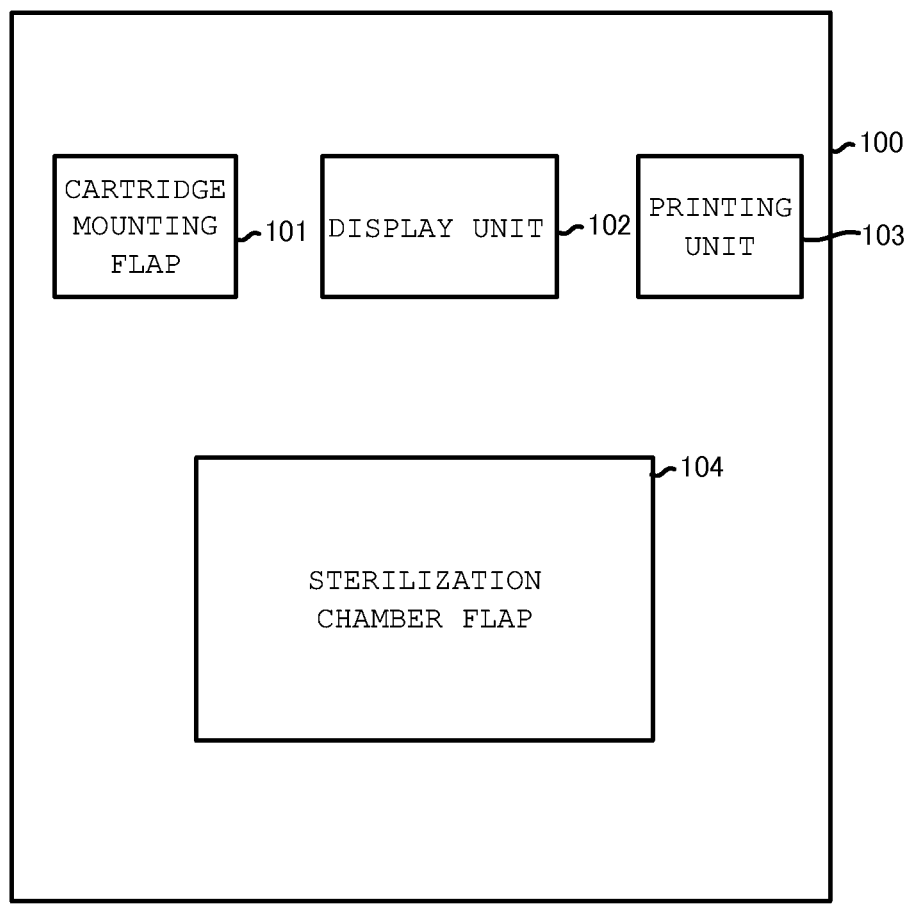
FIG. 1 is a diagram of an external appearance of a sterilization apparatus according to an embodiment of the invention viewed from the front.

FIG. 1 is a diagram of the external appearance of a sterilization apparatus, according to an embodiment of the present invention, as viewed from the front.

The sterilization apparatus 100 according to the present invention includes a cartridge mounting flap 101, a display unit 102, a printing unit 103, and a sterilization chamber flap 104.

The cartridge mounting flap 101 is a flap used for mounting a cartridge, which is a container filled with a sterilizing agent (hydrogen peroxide or liquid hydrogen peroxide solution). When the cartridge mounting flap 101 is opened, there is a cartridge mounting location, and it is possible for a user to mount the cartridge at the location.

The display unit 102 is a touch panel display screen such as a liquid crystal display.

The printing unit 103 is a printer for printing a history of sterilization processes and sterilization results on printing paper, and prints the history of sterilization processes and sterilization results on printing paper as appropriate.

The sterilization chamber flap 104 is a flap for putting a target object for sterilization (object to be sterilized) such as medical equipment into a sterilization chamber to sterilize thereof. When the sterilization chamber flap 104 is opened, there is a sterilization chamber, and it is possible to put a target object for sterilization into the sterilization chamber by inserting the object for sterilization and closing the sterilization chamber flap 104.

The sterilization chamber is a housing with a finite capacity. The pressure within the sterilization chamber can be maintained from an atmospheric pressure to a vacuum pressure. Further, the temperature within the sterilization chamber is maintained at a temperature within a predetermined range, suitable for sterilization, during the sterilization process.

Next, an example of a hardware configuration of the sterilization apparatus according to the present invention will be described using FIG. 2.

Figure 2:
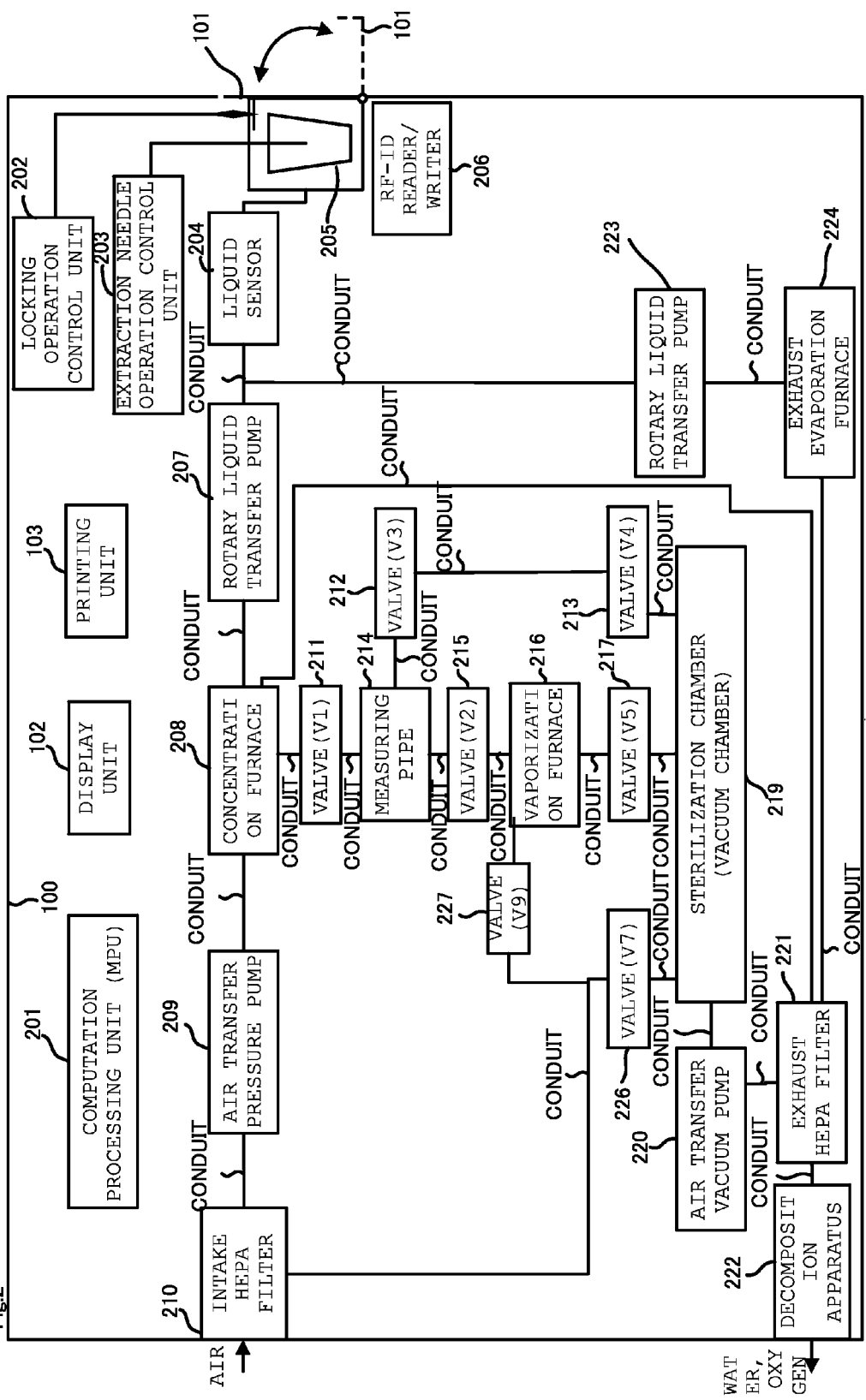
FIG. 2 is a block diagram illustrating an example of a configuration of hardware of the sterilization apparatus according to an embodiment of the invention.

FIG. 2 is a diagram illustrating an example of a hardware configuration of the sterilization apparatus according to an embodiment of the invention.

The sterilization apparatus 100 according to the present invention includes a computation processing unit 201 (for example, micro processing unit (MPU)), a display unit 102, a printing unit 103, a locking operation control unit 202, an extraction needle operation control unit 203, a cartridge mounting flap 101, a liquid sensor 204, cartridges 205, and an RF-ID reader/writer 206, a rotary liquid transfer pump 207, a concentration furnace 208, an air transfer pressure pump 209, an intake HEPA (High Efficiency Particulate Air Filter) filter 210, a valve (V1) 211, a valve (V3) 212, a valve (V4) 213, a measuring pipe 214, a valve (V2) 215, a vaporization furnace 216, a valve (V5) 217, a valve (V9) 227, a valve (V7) 226, a sterilization chamber (also referred to as a vacuum chamber) 219, an air transfer vacuum pump 220, an exhaust HEPA filter 221, a sterilizing agent decomposition apparatus 222, a rotary liquid transfer pump 223, and an exhaust evaporation furnace 224.

The sterilization apparatus 100 is an apparatus that sterilizes an object by taking out a sterilizing agent from the cartridge 205 containing the sterilizing agent.

The computation processing unit 201 (for example, MPU) performs a computation processing and controls each item of hardware of the sterilization apparatus 100.

Since the display unit 102, the printing unit 103 and the cartridge mounting flap 101 have been already described referring to FIG. 1, description thereof will not be repeated.

The locking operation control unit 202, which is a unit that performs a locking and unlocking operation of the cartridge mounting flap 101, prevents the cartridge mounting flap 101 from opening by locking the cartridge mounting flap 101, and further, makes it possible to open the cartridge mounting flap 101 by unlocking the cartridge mounting flap 101.

The cartridge 205 is a sealed container filled with the sterilizing agent (hydrogen peroxide or liquid hydrogen peroxide solution). In addition, the lower side of the cartridge 205 is provided with a RF-ID storage medium, and the storage medium stores a serial number as information that identifies the cartridge (the identification information of the cartridge), the date of manufacturing the cartridge, the date and time at which the cartridge was first used in a sterilization apparatus (date and time of first use) and the remaining amount of sterilizing agent that the cartridge contains.

The RF-ID is a storage medium on which data relating to the disposal of the sterilizing agent (all or any of the serial number, the date of manufacture, the date of first use, and the remaining amount of the sterilizing agent) within the cartridge 205 is stored.

The extraction needle operation control unit 203 is a unit that causes an extraction needle (syringe needle) to be inserted into the cartridge from above so it can suck out the sterilizing agent within the cartridge.

In other words, in the case of inserting the extraction needle (injection needle) for sucking the sterilizing agent in the cartridge into the cartridge from above, it is possible to insert the extraction needle into the cartridge from above (injection needle) by moving the extraction needle (injection needle) downwards toward the cartridge from above the cartridge. In addition, in a case of pulling the extraction needle (injection needle) out from the cartridge, it is possible to pull the extraction needle (injection needle) out from the cartridge by moving the extraction needle (injection needle) up and away from the cartridge.

Although, the cartridge is conveniently located below the extraction needle in this embodiment, it is envisaged that other orientations may also be possible. For example, the extraction needle could be arranged to enter the cartridge from a side wall.

The extraction needle comprises a narrow pipe for sucking out sterilizing agent within the cartridge.

The liquid sensor 204 is a device for detecting whether liquid sterilizing agent from the cartridge 205 is passing through a conduit pipe that is connected between the extraction needle and the rotary liquid transfer pumps 207 and 223. Specifically, whether the sterilizing agent is passing through the pipe can be detected from an optical spectrum obtained by irradiating the pipe with infrared rays.

The RF-ID reader/writer 206 is a device that can read the serial number, the date of manufacture, the date and time of first use, and the remaining amount of sterilizing agent from the RF-ID attached to the bottom of the cartridge 205. Further, the RF-ID reader/writer 206 is a device that can write the date and time of first use and the remaining amount of sterilizing agent to the RF-ID attached to the bottom of the cartridge 205.

In addition, by installing the RF-ID reader/writer 206 at the bottom of the cartridge mounting location behind the cartridge mounting flap 101, it is possible to read the RF-ID attached to the bottom of the cartridge 205, and to write data such as the date and time of first use and the remaining amount of sterilizing agent in the RF-ID.

The rotary liquid transfer pump 207 is connected with the concentration furnace 208 through a conduit pipe, and is also connected via a further conduit with the liquid sensor 204. The rotary liquid transfer pump 207 is an apparatus that sucks out the liquid sterilizing agent within the cartridge 205 through a pump and sends the sterilizing agent to the concentration furnace 208 through the aforementioned conduit pipe between the pump 207 and the furnace 208.

In addition, the rotary liquid transfer pump 207 is capable of suctioning a predetermined amount of sterilizing agent from the cartridge 205 in cooperation with the liquid sensor 204.

The concentration furnace 208 is connected with the rotary liquid transfer pump 207, the air transfer pressure pump 209, the measuring pipe 214, and the exhaust HEPA filter 221 respectively via further conduit pipes. The concentration furnace 208 will be described below referring to FIG. 10. The sterilizing agent fed through the conduit pipe from the rotary liquid transfer pump 207 is concentrated in the furnace 208 by being heated using a heater, thereby vaporizing water contained in the sterilizing agent.

In addition, the vaporized water is pushed out to a conduit pipe which is conducted with the exhaust HEPA filter 221 by air which is fed through a conduit pipe from the air transfer pressure pump 209, and is evacuated from the inside of the concentration furnace 208. In addition, the valve (V1) 211 is provided in a conduit pipe between the measuring pipe 214 and the concentration furnace 208.

The air transfer pressure pump 209 is conducted with the concentration furnace 208 and the intake HEPA filter 210 respectively via conduit pipes. In the air transfer pressure pump 209, the external air of the sterilization apparatus 100 is transferred through the intake HEPA filter 210 to the concentration furnace 208 using a conduit pipe of the intake HEPA filter 210.

The intake HEPA filter 210 is connected with the air transfer pressure pump 209 the sterilization chamber 219 and the vaporization furnace 216 respectively via conduit pipes. The intake HEPA filter 210 performs filtering to exclude dust, dirt, and bacteria in the external air (air) outside the sterilization apparatus 100 using a HEPA filter, thereby cleaning the air. The cleaned air is transferred to the concentration furnace 208 through a conduit pipe by the air transfer pressure pump 209.

In addition, the cleaned air is fed into the vaporization furnace 216 via a conduit pipe of the vaporization furnace 216, and fed into the sterilization chamber 219 via a conduit pipe of the sterilization chamber 219. In other words, the intake HEPA filter 210 is connected to the air in the environment outside of the sterilization apparatus 100.

Therefore, the conduit pipe between the air transfer pressure pump 209 and the intake HEPA filter 210, the conduit pipe between the sterilization chamber 219 and the intake HEPA filter 210, and the conduit pipe between the vaporization furnace 216 and the intake HEPA filter 210 are connected with the air through the intake HEPA filter 210.

In addition, a valve (V9) 227 is provided in a conduit pipe between the vaporization furnace 216 and the intake HEPA filter 210. In addition, a valve (V7) 226 is provided in a conduit pipe between the intake HEPA filter 210 and the sterilization chamber 219.

Valve (V1) 211 is provided in a conduit pipe between the concentration furnace 208 and the measuring pipe 214, and opening the valve (V1) allows fluid communication between the concentration furnace 208 and the measuring pipe 214 through the conduit pipe, whereas closing the valve prevents fluid communication between the concentration furnace 208 and the measuring pipe 214 via the conduit pipe.

The valve (V3) 212 is a valve which is provided in the conduit pipe between the measuring pipe 214 and the sterilization chamber 219. Opening the valve (V3) allows fluid communication between the measuring pipe 214 and the sterilization chamber 219 through the conduit pipe, whereas closing the valve prevents fluid communication between the measuring pipe 214 and the sterilization chamber 219 through the conduit pipe. In addition, this valve (V3) is provided near the measuring pipe 214, and is provided in a position further toward the measuring pipe 214 side than at least the valve (V4) that will be described below.

The valve (V4) 213 is a valve which is provided in the conduit pipe between the measuring pipe 214 and the sterilization chamber 219. Opening the valve (V4) allows fluid communication between the measuring pipe 214 and the sterilization chamber 219 through the conduit pipe, whereas closing the valve prevents fluid communication between the measuring pipe 214 and the sterilization chamber 219 through the conduit pipe. In addition, this valve is provided near the sterilization chamber 219, and is provided in a position further toward the sterilization chamber 219 side than at least the valve (V3) described above.

In the present embodiment, allowing and preventing connection of the conduit pipe between the measuring pipe and the sterilization chamber is performed by opening and closing the valve (V4) 213 and the valve (V3) 212. However, it is possible to allow and prevent conduction of the conduit pipe between the measuring pipe and the sterilization chamber by opening and closing either the valve (V4) 213 or the valve (V3) 212.

Thus, in other embodiments it is possible to allow and prevent conduction of the conduit pipe between the measuring pipe and the sterilization chamber by only providing one of the valve (V4) 213 and the valve (V3) 212 and performing opening and closing that valve.

The measuring pipe 214 is connected with the concentration furnace 208, the vaporization furnace 216, and the sterilization chamber 219 via respective conduit pipes therebetween.

In the measuring pipe 214, the sterilizing agent flows from the concentration furnace 208 as a result of the valve (V1) 211 being opened. Unnecessary air sucked in from inside the cartridge 205 as a result of the valve (V3) 212 and the valve (V4) 213 being opened, and/or unnecessary air that flows into the concentration furnace 208 from the intake HEPA filter 210 and into the measuring pipe 214 from the concentration furnace 208, is removed by the measuring pipe 214. The measuring pipe 214 will be described in more detail below referring to FIG. 10.

The valve (V2) 215 is a valve which is provided in the conduit pipe between the measuring pipe 214 and the vaporization furnace 216, and opening the valve allows fluid communication between the measuring pipe 214 and the vaporization furnace 216 through the conduit pipe, whereas closing the valve prevents fluid communication between the measuring pipe 214 and the vaporization furnace 216 via the conduit pipe.

The vaporization furnace 216 is connected with the measuring pipe 214, the intake HEPA filter 210, and the sterilization chamber 219 via respective conduit pipes therebetween. The vaporization furnace 216 is an example of a vaporization chamber of the present invention.

In the vaporization furnace 216, the sterilizing agent is vaporized by reducing pressure by the air transfer vacuum pump 220.

The valve (V5) 217 is a valve which is provided in the conduit pipe between the vaporization furnace 216 and the sterilization chamber 219, and opening the valve allows fluid communication between the vaporization furnace 216 and the sterilization chamber 219 through the conduit pipe, whereas closing the valve prevents fluid communication between the vaporization furnace 216 and the sterilization chamber 219 through the conduit pipe.

The valve (V9) 227 is a valve which is provided in the conduit pipe between the vaporization furnace 216 and the intake HEPA filter 210, and opening the valve allows fluid communication between the vaporization furnace 216 and the intake HEPA filter 210 through the conduit pipe, whereas closing the valve prevents fluid communication between the vaporization furnace 216 and the intake HEPA filter 210 through the conduit pipe. In other words, the valve (V9) 227 is a valve which can allow and prevent fluid communication between the vaporization furnace 216 and the atmosphere (e.g. air) of the external environment The valve (V7) 226 is a valve which is provided in the conduit pipe between the sterilization chamber 219 and the intake HEPA filter 210, and opening the valve allows fluid communication between the sterilization chamber 219 and the intake HEPA filter 210 through the conduit pipe, whereas closing the valve prevents fluid communication between the sterilization chamber 219 and the intake HEPA filter 210 through the conduit pipe. In other words, the valve (V7) 226 is a valve which can allow and prevent fluid communication between the sterilization chamber 219 and the atmosphere (e.g. air) of the external environment.

The sterilization chamber (also referred to as a vacuum chamber) 219 was also described referring to FIG. 1 and is a housing with a predetermined capacity which sterilizes target objects for sterilization such as equipment for medical treatment. The pressure of the inside of the sterilization chamber can be maintained between atmospheric pressure and vacuum pressure.

Further, the temperature within the sterilization chamber 219 is maintained at a temperature within a predetermined range suitable for sterilization during the sterilization process. Further, a pressure sensor is provided in the sterilization chamber 219, and the pressure within the sterilization chamber 219 can be measured by the sterilization sensor. The sterilization apparatus 100 determines whether the pressure within the sterilization chamber 219 is a predetermined pressure suitable for sterilization using the pressure measured by the pressure sensor.

The air transfer vacuum pump 220 is a device that suctions gases from inside the sterilization chamber 219, the vaporization furnace 216, the measuring pipe 214, the conduit pipe between the measuring pipe 214 and the vaporization furnace 216, the conduit pipe between the vaporization furnace 216 and the sterilization chamber 219, and the conduit pipe between the measuring pipe 214 and the sterilization chamber 219. The air transfer vacuum pump 220 depressurizes thereof to create a vacuum state (the state of a space which is filled with gas at a pressure lower than atmospheric pressure).

The air transfer vacuum pump 220 is conducted with the sterilization chamber 219 via a conduit pipe, and is connected with the exhaust HEPA filter 221 via a conduit pipe.

The exhaust HEPA filter 221 is connected with the air transfer vacuum pump 220 via a conduit pipe. Further, the exhaust HEPA filter 221 is conducted with the exhaust evaporation furnace 224 via a conduit pipe.

In addition, the exhaust HEPA filter 221 is connected with the sterilizing agent decomposition apparatus 222 via a conduit pipe. In addition, the exhaust HEPA filter 221 is connected with the concentration furnace 208 via a conduit pipe.

The exhaust HEPA filter 221 cleans the sucked gas by filtering with the exhaust HEPA filter 221 to exclude dirt, dust, microorganisms, and the like within the gas transferred from a conduit pipe between the air transfer vacuum pump 220 and the exhaust HEPA filter 221 from the gas sucked in from within the sterilization chamber 219 by the air transfer vacuum pump 220.

Further, the cleaned gas that passes through the conduit pipe between the sterilizing agent decomposition apparatus 222 and the exhaust HEPA filter 221, is transferred to the sterilizing agent decomposition apparatus 222. Molecules of the sterilizing agent contained in the gas are decomposed by the sterilizing agent decomposition apparatus 222, and the molecules after decomposition are discharged outside the sterilization apparatus 100.

Further, the exhaust HEPA filter 221 cleans the gas exhausted from the concentration furnace 208 via a conduit pipe between the concentration furnace 208 and the exhaust HEPA filter 221.

This gas substantially comprises vaporized water, from the sterilizing agent vaporized by being heated in the concentration furnace 208. However, since it also contains small amounts of sterilizing agent, it is transferred through the conduit pipe between the sterilizing agent decomposition apparatus 222 and the exhaust HEPA filter 221 to the sterilizing agent decomposition apparatus 222. Further, molecules of sterilizing agent contained in the gas are decomposed by the sterilizing agent decomposition apparatus 222, and the molecules after decomposition are discharged outside the sterilization apparatus 100.

In addition, the exhaust HEPA filter 221 cleans the vaporized sterilizing agent that is transferred through the conduit pipe between the exhaust evaporation furnace 224 and the exhaust HEPA filter 221 from the exhaust evaporation furnace 224. Further, the gaseous cleaned sterilizing agent, is transferred through the conduit pipe between the sterilizing agent decomposition apparatus 222 and the exhaust HEPA filter 221 to the sterilizing agent decomposition apparatus 222. Molecules of sterilizing agent contained in the gas are decomposed by the sterilizing agent decomposition apparatus 222, and the molecules after decomposition are discharged outside the sterilization apparatus 100.

By cleaning the gases sent through conduit pipes, the exhaust HEPA filter 221 can restrain dust and dirt from being accumulated in the sterilizing agent decomposition apparatus 222, and can, therefore, extend the product life of the sterilizing agent decomposition apparatus 222.

The sterilizing agent decomposition apparatus 222 is connected with the exhaust HEPA filter 221 via a conduit pipe. The sterilizing agent decomposition apparatus 222 decomposes molecules of sterilizing agent contained in the gas transferred from the conduit pipe between the sterilizing agent decomposition apparatus 222 and the exhaust HEPA filter 221, and the molecules after decomposition are discharged outside the sterilization apparatus 100.

The sterilizing agent decomposition apparatus 222 is an apparatus for decomposing the sterilizing agent, and is an apparatus that can, for example, in a case where the sterilization agent is hydrogen peroxide or a hydrogen peroxide solution, decompose vaporized hydrogen peroxide into water and oxygen using manganese dioxide as a catalyst.

The rotary liquid transfer pump 223 is connected with the exhaust evaporation furnace 224 via a conduit pipe, and further, is connected with the liquid sensor 204 via a conduit pipe.

In the rotary liquid transfer pump 223, the entire liquid sterilizing agent in the cartridge 205 is suctioned using a pump. The sterilizing agent that is transferred through the conduit pipe between the liquid sensor 204 and rotary liquid transfer pump 223, is transferred through the conduit pipe between the rotary liquid transfer pump 223 and the exhaust evaporation furnace 224 to the exhaust evaporation furnace 224.

The exhaust evaporation furnace 224 is connected with the rotary liquid transfer pump 223 via a conduit pipe, and further, is connected with the exhaust HEPA filter 221 via a conduit pipe.

The exhaust evaporation furnace 224 heats the entire liquid sterilizing agent in the cartridge 205 transferred through the conduit pipe between the rotary liquid transfer pump 223 and the exhaust evaporation furnace 224 using a heater provided in the exhaust evaporation furnace 224, and the entire sterilizing agent is vaporized. Further, the vaporized sterilizing agent is transferred through the conduit pipe between the exhaust HEPA filter 221 and the exhaust evaporation furnace 224 to the exhaust HEPA filter 221.

Next, an example of each step of the sterilization process of the sterilization apparatus according to the present invention will be described referring to FIGS. 4A and 4B.

Figure 4A:
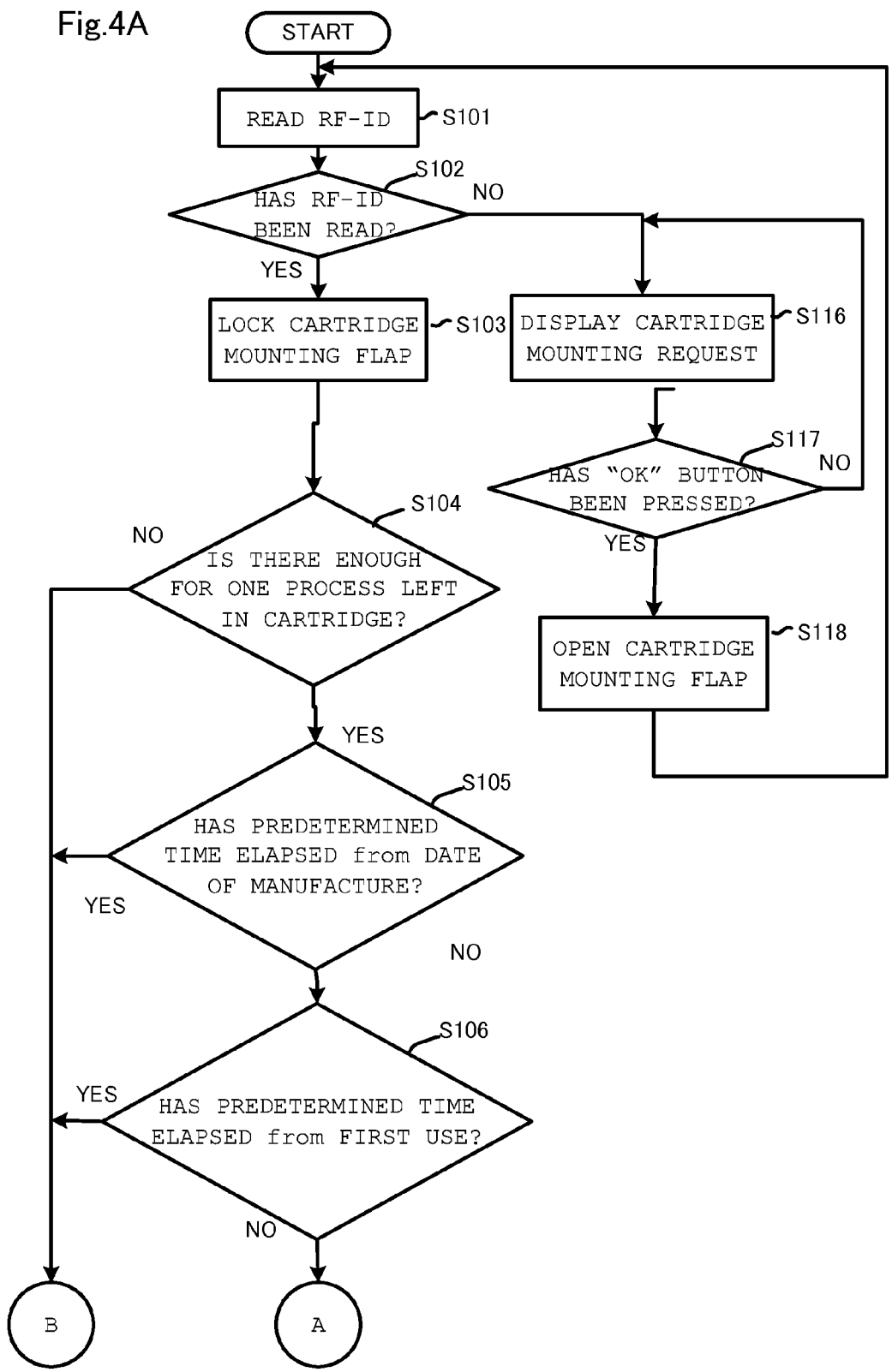
FIGS. 4A and 4B are diagrams illustrating an example of each step of a sterilization process by the sterilization apparatus according to an embodiment of the invention.
Figure 4B:
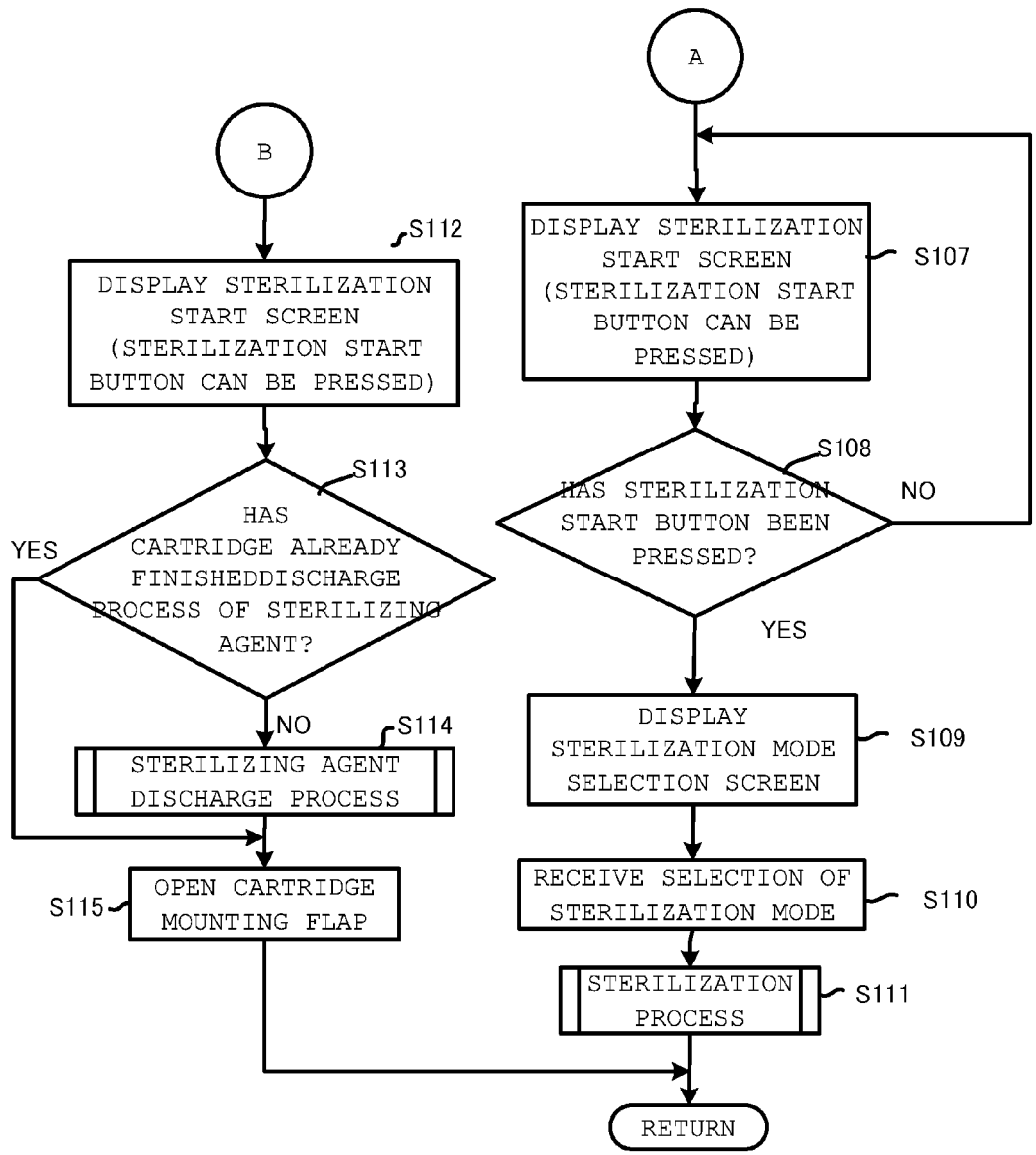

In this embodiment each step of the process illustrated in FIGS. 4A and 4B is preferably performed by controlling the operation of each respective device in the sterilization apparatus using the computation processing unit 201 of the sterilization apparatus 100. That is, by executing a computer-readable program by the computation processing unit 201 of the sterilization apparatus 100, the operation of each apparatus is controlled and each step illustrated in the drawings is executed. FIGS. 4A and 4B are diagrams illustrating an example of each step of the sterilization process by the sterilization apparatus according to an embodiment of the present invention.

In step S101, in the sterilization apparatus 100, when power is turned on, the RF-ID reader/writer 206 (reading unit/writing unit) first reads data from an RF-ID (storage medium) provided on the lower side of the cartridge 205. The RF-ID reader/writer 206 is an example of the reading unit of the present invention.

In step S101, data such as a serial number as information that identifies the cartridge, the date of manufacture of the cartridge, the date and time at which the cartridge was first used in the sterilization apparatus, and the remaining amount of sterilizing agent that the cartridge contains, is read from the RF-ID storage medium.

The serial number, the date of manufacture, the date of first use (date of first use information), and the remaining amount of the sterilizing agent are stored in advance in the RF-ID (i.e. a storage medium) provided on the cartridge 205. The date of first use (date on which the cartridge was first used in the sterilization apparatus) is not stored in the RF-ID of a cartridge to be used in the sterilization for the first time.

Therefore, while the serial number, the date of manufacture, and the remaining amount of the sterilizing agent are stored in the RF-ID of a cartridge used for the first time, the serial number, the date of manufacture, the date of first use, and the remaining amount of the sterilizing agent are stored in the RF-ID of a cartridge used for the second time or after.

Therefore, in step S101, the serial number, the date of manufacture, and the remaining amount of the sterilizing agent are read from the RF-ID of a cartridge to be used for the first time. Further, the serial number, the date of manufacture, the date of first use, and the remaining amount of the sterilizing agent are stored in the RF-ID of a cartridge used for the second time or after.

Therefore, in step S102, even if the date of first use could not be read from the RF-ID of a cartridge used for the first time, if the serial number, the date of manufacture, and the remaining amount of the sterilizing agent can be read, it is determined that data has been read from the RF-ID.

Next, in a case where it is determined that the data has been read from the RF-ID in step S101 (YES in step S102), the sterilization apparatus 100 determines, in step S103, that a cartridge is provided at the mounting location of the cartridge in the sterilization apparatus 100, and the cartridge mounting flap 101 is locked.

That is, locking is performed so that the cartridge cannot be taken out. In such a manner, in a case where data is read at first by the reading unit after the cartridge is mounted on the sterilization apparatus, locking is performed so that the cartridge 205 cannot be taken out.

For example, in one embodiment the cartridge can be made unable to be taken out by not withdrawing a syringe needle inserted into the cartridge.

More specifically, by inserting a syringe needle into the cartridge in step S103, the sterilizing agent within the cartridge can be extracted, and the cartridge can be made unable to be taken out.

In a case where the cartridge is mounted on amounting location of the cartridge on the sterilization apparatus 100 in such a manner, locking is performed so that the cartridge cannot be taken out.

In a case where a cartridge containing remaining sterilizing agent is mounted at the mounting location of the cartridge on the sterilization apparatus 100, since locking is performed so that the cartridge cannot be taken out, the user can be prevented from touching the sterilizing agent.

In a case where the sterilization apparatus 100 has a cartridge mounted on the sterilization apparatus 100 as described above, locking is performed so that the cartridge cannot be taken out. This is an application example of the locking unit of the present invention.

Further, the sterilization apparatus 100 determines whether there is a predetermined amount (for example, 8 ml) of sterilizing agent for one sterilization operation in the cartridge. Specifically, the sterilization apparatus 100 determines whether the remaining amount of sterilizing agent obtained from the RF-ID is greater than a predetermined amount for one sterilization operation.

That is, in a case where the remaining amount of sterilizing agent is determined to be greater than a predetermined amount for one sterilization operation, it is determined that there is a predetermined amount of sterilizing agent (sufficient sterilization process can be performed) for one sterilization operation in the cartridge (YES in step S104), and the processing proceeds to step S105. On the other hand, in a case where the remaining amount of sterilizing agent is determined to be less than the predetermined amount (for example, 8 ml) for one sterilization operation, it is determined there is not a predetermined amount of sterilizing agent (sufficient sterilization process cannot be performed) for one sterilization operation in the cartridge (NO in step S104), and the processing proceeds to step S112.

In step S105, the sterilization apparatus 100 determines whether a predetermined period of time (for example, 13 months) has elapsed from the date of manufacture of the cartridge obtained from the RF-ID.

Further, in a case where it is determined that the predetermined period of time has elapsed since the date of manufacture (YES in step S105), it is determined that a sufficient sterilization process cannot be executed, and the processing proceeds to step S112. On the other hand, in a case where it is determined that the predetermined period has not elapsed since the date of manufacture (NO in step S105), it is determined that a sufficient sterilization process can be executed, and the processing proceeds to step S106.

In step S106, the sterilization apparatus 100 determines from the date of first use obtained from the RF-ID whether a predetermined period of time (for example, two weeks) has elapsed. Therefore, since the date of first use is not read from the RF-ID of a cartridge used for the first time in step S101, it is determined in step S106 from the date of first use obtained from the RF-ID that the predetermined period of time has not elapsed (NO in step S106).

Further, in a case where it is determined that the predetermined period of time has elapsed since the date and time of first use obtained from the RF-ID (YES in step S106), it is determined that a sufficient sterilization process cannot be executed, and the processing proceeds to step S112d. On the other hand, in a case where it is determined that the predetermined period of time has not elapsed (NO in step S106), it is determined that a sufficient sterilization process can be executed, and the processing proceeds to step S107.

Figure 3:
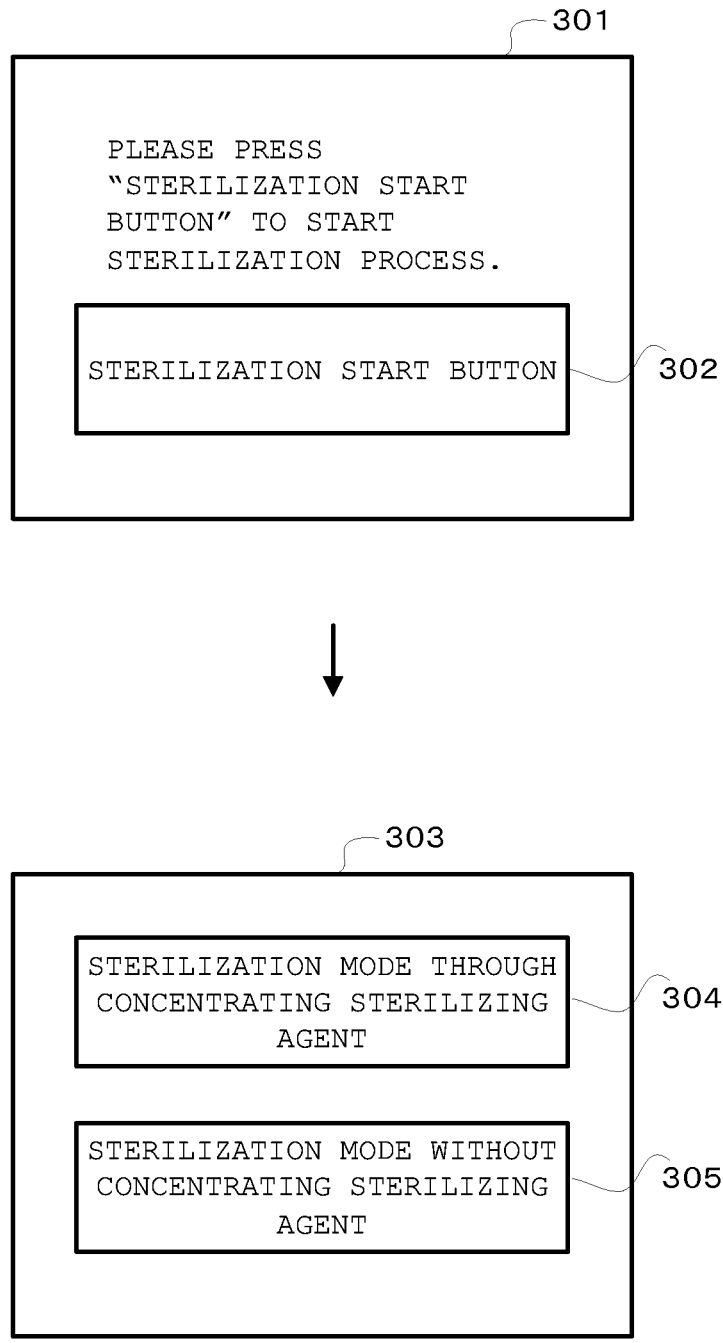
FIG. 3 is a diagram illustrating an example of a screen displayed on a display unit 102 of a sterilization apparatus 100.

In step S107, the sterilization apparatus 100 displays a sterilization start screen 301 in FIG. 3 on the display unit 102.

FIG. 3 is a diagram illustrating an example screen that is displayed on the display unit 102 of the sterilization apparatus 100.

A "sterilization start button" is displayed on the sterilization start screen 301. The "sterilization start button" 302 on the sterilization start screen 301 displayed in step S107, is operable by a user (active).

Furthermore, when the "sterilization start button" 302 is pressed by the user (YES in step S108), the sterilization apparatus 100 displays the sterilization mode selection screen 303 in FIG. 3 on the display unit 102.

A "sterilization mode through concentrating sterilizing agent" button 304 and a "sterilization mode without concentrating sterilizing agent" button 305 are displayed on the sterilization mode selection screen 303.

The sterilization apparatus 100 receives a selection from a user of either the "sterilization mode through concentrating sterilizing agent" button 304 or the "sterilization mode without concentrating sterilizing agent" button 305 in step S110, and performs a sterilization process according to the mode of the button selected by the user in step S111. Details of the sterilization processes in step S111 will be described below referring to FIG. 5.

In this manner, according to the instruction of a user, it is possible to switch the mode of a sterilization process in one sterilization apparatus. That is, in a case where the "sterilization mode through concentrating sterilizing agent" button 304 is pressed by a user, the sterilizing agent is concentrated and a sterilization process is performed, and in a case where the "sterilization mode without concentrating sterilizing agent" button 305 is pressed by a user, the sterilizing agent is not concentrated and a sterilization process is performed.

Then, at the end of the sterilization process in step S111, the sterilization apparatus 100 returns the process to step S101.

In addition, in step S112, the sterilization apparatus 100 displays the sterilization start screen 301 in FIG. 3 on the display unit 102. However, the "sterilization start button" 302 on the sterilization start screen 301 in FIG. 3 displayed in step S112, is made inoperable and is displayed in such a manner that it indicates that it cannot be pressed by a user ("sterilization start button" 302 is not active). Therefore, it is possible to ensure that an instruction to start the sterilization process by a user is not accepted.

In addition, in step S113, the sterilization apparatus 100 determines whether the cartridge mounted in the cartridge mounting location is a cartridge from which the sterilizing agent has already been fully discharged, using the serial number obtained in from the RF-ID in step S101.

Specifically, serial numbers that identify cartridges from which the sterilizing agent has already been fully discharged are stored in the memory (storage unit) of the sterilization apparatus 100, and it is determined whether the cartridge currently installed in the sterilization apparatus 100 is a cartridge from which the sterilizing agent has already been fully discharged by determining whether the serial number obtained from the RF-ID in step S101 matches a serial number stored in memory (storage unit).

Further, other examples of determining whether a cartridge has finished the discharge process of the sterilizing agent will be described here.

When the sterilizing agent discharge process in step S114 is performed, the sterilization apparatus 100 records information indicating that a cartridge has already finished the discharge process of the sterilizing agent is recorded in the RF-ID of the cartridge 205.

Further, in step S113, the sterilization apparatus 100 determines whether reading information indicating that a cartridge has already finished the discharge process of the sterilizing agent has been performed in step S101. In a case where it is determined that reading of the information has been performed (YES in step S113), the processing proceeds to step S115, and in a case where it is determined that the reading of the information has not been read (NO in step S113), the processing proceeds to step S114.

In such a manner, it is also possible to determine whether the cartridge currently mounted on the sterilization apparatus 100 is a cartridge that has already finished the discharge process of the sterilizing agent.

In a case where it is determined that the cartridge currently installed in the sterilization apparatus 100 is a cartridge from which the sterilizing agent has already been fully discharged (YES in step S113), the processing proceeds to step S115. On the other hand, in a case where it is determined that the cartridge is not a cartridge from which the sterilizing agent has already been fully discharged (NO in step S113), a sterilizing agent discharge process in step S114 is performed in which the entire remaining liquid sterilizing agent in the cartridge is suctioned, undergoes a decomposition process, and is discharged outside the sterilization apparatus 100. And thereafter, the process of step S115 is performed. The details of the discharge process of step S114 will be described below referring to FIG. 9.

Step S114 is an application example of the disposal unit for disposing of the hydrogen peroxide solution within the cartridge. That is, the disposal unit disposes of the entire hydrogen peroxide within the cartridge through decomposition using a catalyst.

In a case where it is determined that the data read in step S101 satisfies predetermined conditions in steps S104, S105, and S106, the sterilizing agent within the cartridge 205 is disposed of by the disposal unit.

Herein, the predetermined conditions are conditions including the condition of whether an amount of sterilizing agent to be used in one sterilizing agent remaining within the cartridge, the condition of whether a predetermined period of time has elapsed since the date of manufacture of the cartridge, and the condition of whether a predetermined period of time has elapsed since the date of first use of the cartridge.

Once the process in step S114 is performed, the serial number read in step S101 is recorded as a serial number for identifying a cartridge that has already finished the discharge process (disposal process) of the sterilizing agent in the memory (storage unit) within the sterilization apparatus 100.

In step S115, the sterilization apparatus 100 unlocks the cartridge mounting flap 101. Step S115 is an application example of the releasing unit releasing the lock by the locking unit. For example, the lock can be released by withdrawing the syringe needle inserted into the cartridge from the cartridge.

In such a manner, since a process of sucking out and disposing of the entire sterilizing agent within the cartridge 205 in step S114 is performed before the lock is released, the user is prevented from touching the sterilizing agent, thereby improving safety.

In addition, in step S102, in a case where it is determined that data could not be read from the RF-ID in step S101 (NO in step S102), it is determined that a cartridge is not installed in the cartridge mounting location of the sterilization apparatus 100. Then, the sterilization apparatus 100, in step S116, displays a cartridge mounting request screen 1101 illustrated in FIG. 11.

Figure 11:
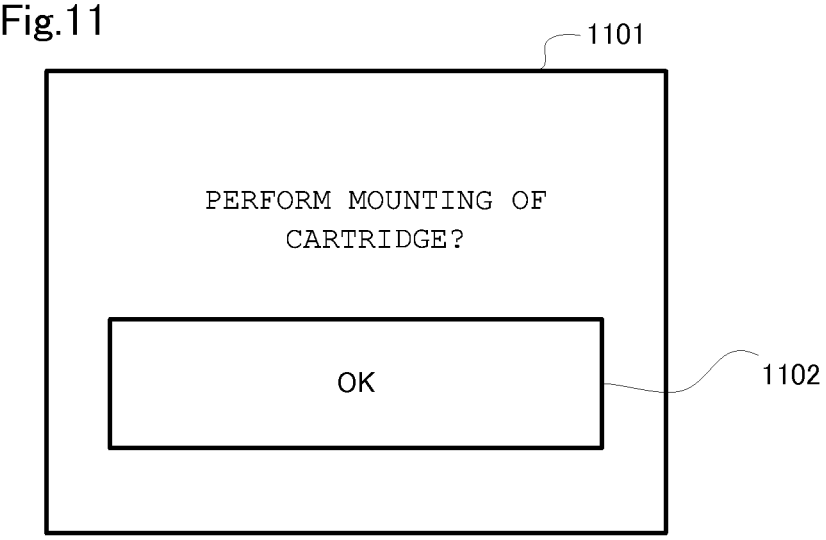
FIG. 11 is a diagram illustrating an example of a cartridge mounting request screen 1101 displayed on the display unit 102 of the sterilization apparatus 100.

FIG. 11 is a diagram illustrating an example of the cartridge mounting request screen 1101 displayed on the display unit 102 of the sterilization apparatus 100. The cartridge mounting request screen 1101 includes an "OK" button 1102.

Further, in step S117, the sterilization apparatus 100 determines whether the "OK" button 1102 on cartridge mounting request screen 1101 has been pressed by a user, and in a case where the "OK" button 1102 has been pressed (YES in step S117), the cartridge mounting flap 101 is unlocked in step S118, and the processing returns to step S101. On the other hand, in a case where the "OK" button 1102 has not been pressed (NO in step S117), display of the cartridge mounting request screen 1101 is kept displaying.

Unlocking and locking of the cartridge mounting flap 101 are performed by an operation of the locking operation control unit 202.

Figure 5:
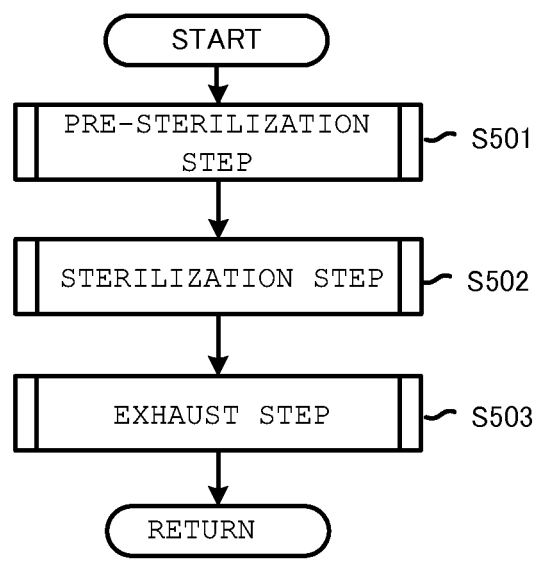
FIG. 5 is a diagram illustrating an example of detailed processing of the sterilization process illustrated in step S111 of FIG. 4B.

Next, referring to FIG. 5, an example of detailed processing of the sterilization process illustrated in step S111 of FIG. 4B will be described in detail. FIG. 5 is a diagram illustrating an example of detailed processing of the sterilization process illustrated in step S111 of FIG. 4B.

Each step (process) illustrated in FIG. 5 is performed by controlling the operation of each apparatus within the sterilization apparatus through the computation processing unit 201 of the sterilization apparatus 100. That is, the operation of each apparatus is preferably controlled by executing a computer-readable program by the computation processing unit 201 of the sterilization apparatus 100, and each step (process) illustrated in FIG. 5 is executed.

When starting the process in step S501 illustrated in FIG. 5, all valves of the sterilization apparatus 100 (the valve (V1) 211, the valve (V2) 215, the valve (V3) 212, the valve (V4) 213, the valve (V9) 227, and the valve (V7) 226) are in a closed state.

Further, in step S501, the sterilization apparatus 100 performs process of a pre-sterilization step of reducing the pressure within the sterilization chamber 219 to a predetermined pressure (for example, 45 Pa) by operating the air transfer vacuum pump 220 and sucking out the gas within the sterilization chamber 219. The detailed process of the pre-sterilization step will be described below referring to FIG. 6.

Further, in step S502, the sterilization apparatus 100 places the sterilizing agent into the sterilization chamber 219 and performs the process of a sterilization step that sterilizes sterilization object. The processing of the sterilization step will be described below in detail referring to FIGS. 7A, 7B, 7C, and 7D.

Next, in step S503, the sterilization apparatus 100 performs the processing of an exhaust step for removing sterilizing agent contained in the sterilization chamber 219 and the vaporization furnace 216. The processing of the exhaust step will be described below in detail referring to FIG. 8.

Figure 6:
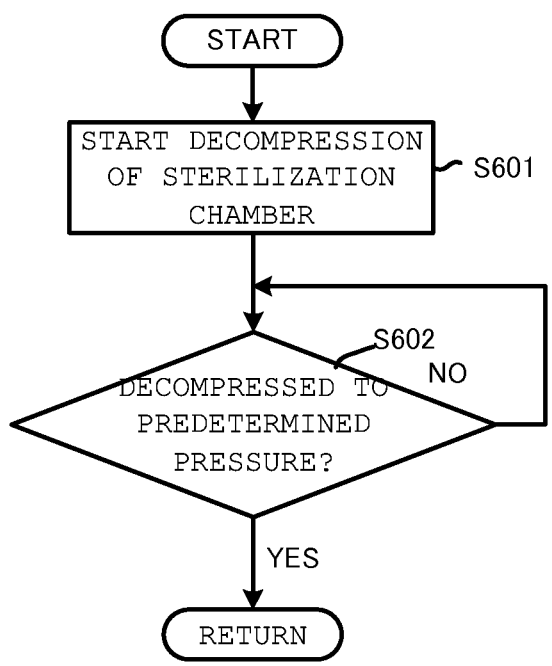
FIG. 6 is a diagram illustrating an example of detailed processing of a pre-sterilization step illustrated in step S501 of FIG. 5l.

Next, referring to FIG. 6, an example of detailed processing of the pre-sterilization step illustrated in step S501 of FIG. 5 will be described. FIG. 6 is a flowchart illustrating an example of the processing of the pre-sterilization step illustrated in step S501 of FIG. 5.

Each step (process) illustrated in FIG. 6 is performed by controlling the operation of each apparatus within the sterilization apparatus through the computation processing unit 201 of the sterilization apparatus 100. That is, each step (process) illustrated in FIG. 6 is preferably executed by controlling the operation of each apparatus by executing a computer-readable program by the computation processing unit 201 of the sterilization apparatus 100.

First, in step S601, the sterilization apparatus 100 operates the air transfer vacuum pump 220 and starts a process of suctioning the gas in the sterilization chamber 219.

Furthermore, in step S602, the sterilization apparatus 100 determines whether the pressure within the sterilization chamber 219 has been reduced to a predetermined pressure (for example, 45 Pa). Specifically, the sterilization apparatus 100 determines whether the pressure within the sterilization chamber 219 measured by a pressure sensor provided in the sterilization chamber 219 has been reduced to a predetermined pressure (for example, 45 Pa).

In step S602, in a case where it is determined that the pressure in the sterilization chamber 219 has not been reduced to the predetermined pressure (for example, 45 Pa) (NO in step S602), the operation of the air transfer vacuum pump 220 is continued, the gas in the sterilization chamber 219 is suctioned and the pressure in the sterilization chamber 219 is reduced.

On the other hand, in step S602, in a case where it is determined that the pressure in the sterilization chamber 219 has been reduced to the predetermined pressure (for example, 45 Pa) (YES in step S602), the operation of the air transfer vacuum pump 220 is continued, the gas in the sterilization chamber 219 is suctioned and the processing of step S502 is started.

Next, referring to FIGS. 7A, 7B, 7C, and 7D, an example of detailed processing of the sterilization step S502 of FIG. 5 will be described.

FIGS. 7A, 7B, 7C, and 7D are diagrams illustrating an example of detailed processing of the sterilization step S502 of FIG. 5. Each step (process) illustrated in FIGS. 7A, 7B, 7C, and 7D is performed by controlling the operation of each apparatus within the sterilization apparatus through the computation processing unit 201 of the sterilization apparatus 100. That is, each step (process) illustrated in the drawing is preferably executed by controlling the operation of each apparatus by executing a computer-readable program by the computation processing unit 201 of the sterilization apparatus 100.

First, in step S701, the sterilization apparatus 100 opens the valve (V5) 217 to allow connection of the conduit pipe between the sterilization chamber 219 and the vaporization furnace 216. Thus, in step S702, since the gas in the sterilization chamber 219 is being suctioned and depressurized by the air transfer vacuum pump 220, depressurization in the sterilization chamber 219 and the vaporization furnace 216 is started.

Further, in step S703, the sterilization apparatus 100 determines which of the "sterilization mode through concentrating sterilizing agent" button 304 and the "sterilization mode without concentrating sterilizing agent" button 305 was pressed in step S110. In a case where it is determined that the "sterilization mode through concentrating sterilizing agent" button 304 was pressed (YES in step S703), the processing proceeds to step S704, and in a case where it is determined that the "sterilization mode without concentrating sterilizing agent" button 305 was pressed (NO in step S703), the processing proceeds to step S728.

Herein, first, a case where the "sterilization mode through concentrating sterilizing agent" button 304 (a case where the sterilizing agent is concentrated and a sterilization process is performed) was pressed will be described.

In step S704, the sterilization apparatus 100 operates the rotary liquid transfer pump 207, and suctions a predetermined amount (for example, 2 ml) of the sterilizing agent in the cartridge 205. Further, the predetermined amount of sterilizing agent that was suctioned is input into the concentration furnace 208. Here, the predetermined amount of sterilizing agent that is suctioned is, for example, an amount that is capable of causing a state of the sterilizing agent in the space of the sterilization chamber 219 to be saturated.

Further, in step S705, the sterilization apparatus 100 writes the remaining amount of sterilizing agent within the cartridge 205 into the RF-ID of the cartridge 205 installed in the cartridge mounting location in the cartridge. Specifically, a value calculated by subtracting the predetermined amount (for example, 2 ml) that was drawn out of the cartridge 205 in step S704 from the remaining amount of sterilizing agent in the cartridge 205 that was read in step S101, is stored in the RF-ID.

That is, in step S705, a value generated by subtracting the total amount of sterilizing agent suctioned out from the cartridge 205 in step S704 from the remaining amount of the sterilizing agent within the cartridge 205 read in step S101, is stored in the RF-ID. In this way, the sterilization apparatus updates the data stored in the storage medium (updating means).

Further, the sterilization apparatus 100 determines that a cartridge is first used this time in the sterilization apparatus in a case where information indicating the date is not included in the date of first use (date when the cartridge was first used in the sterilizing agent) read from the RF-ID in step S101. That is, the sterilization apparatus 100 determines that a cartridge is first used in the sterilization this time in a case where the date of first use could not be read from the RF-ID in step S101.

In only a case where it is determined that this time is the first use of a cartridge in a sterilization apparatus, current date and time information is also written into the RF-ID.

Next, in step S706, since the sterilization apparatus 100 constantly heats the heater provided in the concentration furnace 208 when the power of the sterilization apparatus 100 is on, the sterilizing agent input into the concentration furnace 208 in step S704 is heated by the heat of the heater and the moisture contained in the sterilizing agent in the concentration furnace 208 is evaporated.

The heater provided in the concentration furnace 208 is constantly heated while the power of the sterilization apparatus 100 is on so that it is possible to use the sterilization apparatus immediately at anytime in an operating room or the like. Thus, by eliminating the time taken to heat the heater of the concentration furnace, it is possible to use the sterilization apparatus immediately at any time.

In other words, in a case where the sterilizing agent is hydrogen peroxide (also referred to as aqueous solution of hydrogen peroxide), the heater provided in the concentration furnace 208 is specifically, for example, warmed to 80° C. Thus, it is possible to largely evaporate (vaporize) moisture and concentrate the sterilizing agent.

Next, in step S707, the sterilization apparatus 100 determines whether a predetermined period of time (for example, 6 minutes) has elapsed since the sterilizing agent was input into the concentration furnace 208 in step S704. Further, when it is determined that the predetermined period of time has elapsed since the sterilizing agent was input into the concentration furnace 208 (YES in step S707), the processing proceeds to step S708. On the other hand, in a case where it is determined that a predetermined period of time has not elapsed since the sterilizing agent was input into the concentration furnace 208 (NO in step S707), the sterilizing agent is left in the concentration furnace 208 and concentration of the sterilizing agent is continued.

Further, in step S708, the sterilization apparatus 100 determines whether the pressure in the sterilization chamber 219 and the vaporization furnace 216 has been reduced to a predetermined pressure (for example, 500 Pa).

Further, in a case where the pressure in the sterilization chamber 219 and the vaporization furnace 216 has been reduced to the predetermined pressure (YES in step S708), then in step S709, by opening the valve (V3) 212 and the valve (V4) 213 for a predetermined period of time (opening the valve (V3) 212 and the valve (V4) 213 for a predetermined period of time (for example, 3 seconds) and then closing the valve (V3) 212 and the valve (V4) 213), the sterilization apparatus 100 depressurizes the measuring pipe 214. On the other hand, in a case where the pressure in the sterilization chamber 219 and the vaporization furnace 216 have not been reduced to the predetermined pressure (NO in step S708), concentration of the sterilizing agent is continued.

Further, next, in step S710, when the sterilization apparatus 100 opens the valve (V1) for a predetermined period of time (for example, 3 seconds) after opening the valve (V3) 212 and the valve (V4) 213 for a predetermined period of time (for example, 3 seconds) and then closing the valve (V3) 212 and the valve (V4) 213 in step S709, since the pressure in the measuring pipe 214 is lower than pressure in the concentration furnace 208 (external), the sterilizing agent in the concentration furnace 208 is drawn into the measuring pipe 214.

Here, by opening the valve (V1) for a predetermined period of time and then closing the valve (V1), the sterilizing agent in the concentration furnace 208 is drawn into the measuring pipe 214. Here, not only the sterilizing agent, but also the air in the concentration furnace 208 is drawn into the measuring pipe 214.

Further, even after this, depressurization of the sterilization chamber 219 continues by the air transfer vacuum pump 220.

Therefore, the pressure in the sterilization chamber 219 is lower than the pressure in the measuring pipe. Specifically, the pressure in the sterilization chamber 219 is approximately 400 Pa and the pressure in the measuring pipe is a value that is approximately atmospheric pressure (101325 Pa). Since the air in the concentration furnace 208 is drawn into the measuring pipe 214 along with the sterilizing agent, the pressure in the measuring pipe rises to almost atmospheric pressure.

Next, in step S711, the sterilization apparatus 100 opens the valve (V3) 212 and the valve (V4) 213 for a predetermined period of time (for example, 3 seconds) and the air (liquid sterilizing agent not included) in the measuring pipe is drawn out into the sterilization chamber 219. That is, here, the valve (V3) 212 and the valve (V4) 213 are opened and once the predetermined period of time has elapsed, the valve (V3) 212 and the valve (V4) 213 are closed.

Next, the sterilization apparatus 100 determines whether the pressure in the sterilization chamber 219 and the vaporization furnace 216 has been depressurized to a predetermined pressure (for example, 80 Pa) and in a case where it is determined that the pressure has been reduced in step S712, the valve (V5) 217 is closed in step S713.

Further, in step S714, the sterilization apparatus 100 opens the valve (V2) 215. Thus, the sterilizing agent in the measuring pipe 214 is drawn into the vaporization furnace 216, and is vaporized in the vaporization furnace 216. Here, the sterilizing agent is vaporized in the vaporization furnace as molecular clusters.

The volume of the sterilization chamber is greater than that of the vaporization furnace, and thus, in the vaporization furnace, the sterilizing agent is vaporized as molecular clusters. The reason for this is that, since the volume of the vaporization furnace is less than that of the sterilization chamber, the distance between molecules of the sterilizing agent in the sterilization chamber is small and there is a tendency for molecular clusters to form as a result of intermolecular forces.

At this time, suctioning of gas in the sterilization chamber 219 using the air transfer vacuum pump 220 continues and the pressure in sterilization chamber 219 is reduced. The pressure inside the vaporization furnace 216 into which the sterilizing agent in the measuring pipe 214 was drawn, rises. In other words, the pressure in the vaporization furnace 216 is higher than the pressure in the sterilization chamber 219.

Next, in step S715, sterilization apparatus 100 determines whether the pressure in the sterilization chamber 219 has been reduced to a predetermined pressure (for example, 50 Pa) and whether the predetermined period of time has elapsed since the valve (V2) 215 was opened in step S714, and in a case where the pressure in the sterilization chamber 219 has been reduced to a predetermined pressure (for example, 50 Pa) and the predetermined period of time has elapsed since the valve (V2) 215 was opened in step S714 (YES in step S715), the suctioning (vacuuming) of the sterilization chamber 219 using the air transfer vacuum pump 220 is stopped in step S716, and the valve (V5) 217 is opened in step S717.

Thus, the sterilizing agent vaporized in the sterilization chamber 219 is diffused and it is possible to sterilize target objects for sterilization.

The sterilizing agent diffuses as a result of the pressure in the sterilization chamber 219 (for example, 50 Pa) being lower than the pressure in the vaporization furnace 216. Here, since it is possible to further subdivide the molecular clusters in the vaporization furnace and cause the sterilizing agent to diffuse in the sterilization chamber to a greater extent, it is possible to improve the sterilizing action of the sterilizing agent. In addition, it is possible to effectively sterilize fine cavities of target objects for sterilization.

Further, it is determined whether a predetermined period of time (for example, 330 seconds) has elapsed since the valve (V5) 217 was opened in step S717 and when it is determined that the predetermined period of time has elapsed since the valve (V5) 217 was opened (YES in step S718), the valve (V9) 227 is opened in step S719.

Thus, since the pressure in the vaporization furnace 216 and the sterilization chamber 219 is lower than the pressure outside the sterilization apparatus 100, external air from outside the sterilization apparatus 100, which has been cleaned by the intake HEPA filter, is drawn into the vaporization furnace 216.

Further, the sterilizing agent in the vaporization furnace 216 that has been charged as gas by the air that was fed into the vaporization furnace 216 and the sterilizing agent that has adhered to the inner surfaces of the vaporization furnace 216, are fed into the sterilization chamber 219, and the sterilizing action on the target objects for sterilization in the sterilization chamber 219 is increased. That is, for example, as a result of this, the sterilizing effect on portions which are difficult to sterilize such as the insides of thin tubes of target objects for sterilization is increased.

Furthermore, when a predetermined period of time (15 seconds) has elapsed since the valve (V9) 227 is opened in step S719, external air from outside the sterilization apparatus 100 cleaned by the intake HEPA filter 210 being suctioned into the sterilization chamber 219 by the sterilization apparatus 100 further opening the valve (V7) 226.

Since the pressure in the sterilization chamber 219 and the vaporization furnace 216 is lower than the pressure outside the sterilization apparatus 100, external air (air) outside the sterilization apparatus 100 is suctioned into the sterilization chamber 219. Thereby, the sterilization effect for portions that are hard to sterilize (particularly the inner cavity) such as the deep portions and thin tubes and the like that are sterilization targets.

Next, the sterilization apparatus 100 determines whether the pressure in the vaporization furnace 216 and the sterilization chamber 219 has risen to the atmospheric pressure, and in a case where it is determined that the pressure has risen to the atmospheric pressure (YES in step S721), the valve (V2) 215 is closed in step S722.

Next, the sterilization apparatus 100 closes the valve (V7) 226 in step S723 and restarts the suctioning (e.g. vacuuming) of the sterilization chamber 219 using the air transfer vacuum pump 220 in step S724. As a result of this, external air from outside the sterilization apparatus 100, which has been cleaned by the intake HEPA filter 210, is drawn into the vaporization furnace 216 through the conduit pipe between the vaporization furnace 216 and the intake HEPA filter 210.

Furthermore, through the air sent into the vaporization furnace 216, the sterilizing agent accumulating as gas within the vaporization furnace 216 and the sterilizing agent attached to the surface on the inside of the vaporization furnace 216 are sent into the sterilization chamber 219.

As a result of this, in addition to increasing the sterilizing action on portions which are difficult to sterilize (particularly cavity portions) such as the insides of thin tubes of target objects for sterilization, it is possible to effectively reduce the sterilizing agent in the vaporization furnace 216.

Further, after a predetermined period of time (for example, 15 seconds) since the suctioning (vacuuming) of the sterilization chamber 219 using the air transfer vacuum pump 220 is resumed in step S724, the sterilization apparatus 100 closes the valve (V9) 227 in step S725.

At this time, suctioning (e.g. vacuuming) of the sterilization chamber 219 using the air transfer vacuum pump 220 is still continued, in step S702, the sterilization chamber 219 and the vaporization furnace 216 are sealed, and, in step S726, the sterilization chamber 219 and the vaporization furnace 216 are depressurized.

Next, in step S727, the sterilization apparatus 100 determines whether the processing from steps S702 to S726 have been executed a predetermined number of times (for example, four times), and in a case where it is determined that the processing have been executed the predetermined number of times (YES in step S727), the sterilization apparatus 100 performs the process of step S503. On the other hand, in a case where it is determined that the processing from steps S702 to S726 have not been executed the predetermined number of times (NO in step S727), the processing from step S702 and subsequent steps are performed again. In such a manner, by executing the processing from steps S702 to S726 a predetermined number of times, the effect of the sterilization action with respect to the sterilization target is enhanced, and the sterilization target can be sufficiently sterilized.

Next, in a case where it is determined that the "sterilization mode without concentrating sterilizing agent" button 305 is pressed in step S703 (a case of performing sterilization without concentrating the sterilizing agent) will be described.

In step S728, in a case where it is determined that the "sterilization mode without concentrating sterilizing agent" button 305 is pressed (NO in step S703), the sterilization apparatus 100 determines whether the pressure in the sterilization chamber 219 and the vaporization furnace 216 has been reduced to a predetermined pressure (for example, 1000 Pa).

Further, in a case where it is determined that the pressure in the sterilization chamber 219 and the vaporization furnace 216 has been reduced to the predetermined pressure (YES in step S728), the sterilization apparatus 100 operates the rotary liquid transfer pump 207 and draws out a predetermined amount (for example, 2 ml) of the sterilizing agent in the cartridge 205, thereby the predetermined amount of sterilizing agent that was drawn out is put into the concentration furnace 208 in step S729.

Here, the predetermined amount of sterilizing agent that is drawn out is, for example, an amount that is capable of achieving a saturated state of the sterilizing agent in the space in the sterilization chamber 219.

Next, in step S730, the sterilization apparatus 100 writes the remaining amount of sterilizing agent in the cartridge 205 into the RF-ID of the cartridge 205 attached in the cartridge mounting location in the cartridge. Specifically, a value that is calculated by subtracting the predetermined amount (for example, 2 ml) that was drawn out of the cartridge 205 in step S729 from the remaining amount of sterilizing agent in the cartridge 205 that was read in step S101, is stored in the RF-ID. In this way, the sterilization apparatus updates the data stored in the storage medium (updating means).

Further, in a case where the predetermined amount of sucking out the sterilizing agent from the cartridge 205 for one time is 2 ml, for example, it is determined in step S727 that the process has not been executed the predetermined number of times (NO in step S727), and in a case where it is the second time, for example, that the processing in step S702 and subsequent steps are performed, since the total amount of sterilizing agent sucked out from the cartridge 205 in step S729 (2 ml (predetermined amount)×twice=) is 4 ml. Therefore, in step S730, the value calculated by subtracting 4 ml that is the total amount of sterilizing agent sucked out from the cartridge 205 in step S729 from the remaining amount of the sterilizing agent within the cartridge 205 read in step S101 is stored into the RF-ID.

That is, in step S730, the value calculated by subtracting the total amount of sterilizing agent sucked out from the cartridge 205 in step S729 from the remaining amount of the sterilizing agent within the cartridge 205 read in step S101 is stored in the RF-ID.

In addition, in step S730, in a case where information indicating date and time is not contained in the date and time of first use (the date and time at which the cartridge was first used in a sterilization apparatus) read from the RF-ID in step S101, it is determined that it is the first use of the cartridge in a sterilization apparatus 100 this time. In other words, in a case where the date of first use could not be read from the RF-ID in step S101, the sterilization apparatus 100 determines that the cartridge is used for the first time.

Only in the case where it is determined that it is the first use of a cartridge in a sterilization apparatus this time, current date and time information is also written into the RF-ID. Further, when the sterilization apparatus 100 performs the process in step S730, the processing of the steps from step S709 and subsequent steps, which have already been described, are performed.

In step S728, if the pressure in the sterilization chamber 219 reaches a predetermined pressure (for example, 1000 Pa), since sucking of the sterilizing agent is started in step S729 and the pressure will have dropped below 500 Pa when sucking of the sterilizing agent is finished in step S729, it is possible to transition to step S709 efficiently.

In such a manner, after the pressure within the sterilization chamber 219 and the vaporization furnace 216 is reduced to a predetermined pressure (for example, 1000 Pa) to start the decompression of the measuring pipe 214, since the predetermined amount of sucked out sterilizing agent is placed in the concentration furnace 208, the measuring pipe 214 can be immediately decompressed in step S709, and the sterilizing agent within the concentration furnace 208 is then placed in the measuring pipe, it is possible to immediately place the sterilizing agent into the measuring pipe 214 from the concentration furnace 208 in step S710. That is, the sterilization can be placed in the measuring pipe 214 without being substantially concentrated in the concentration furnace 208.

Next, referring to FIG. 8, an example of detailed processing of the exhaust step illustrated in step S503 of FIG. 5 will be described.

Figure 8:
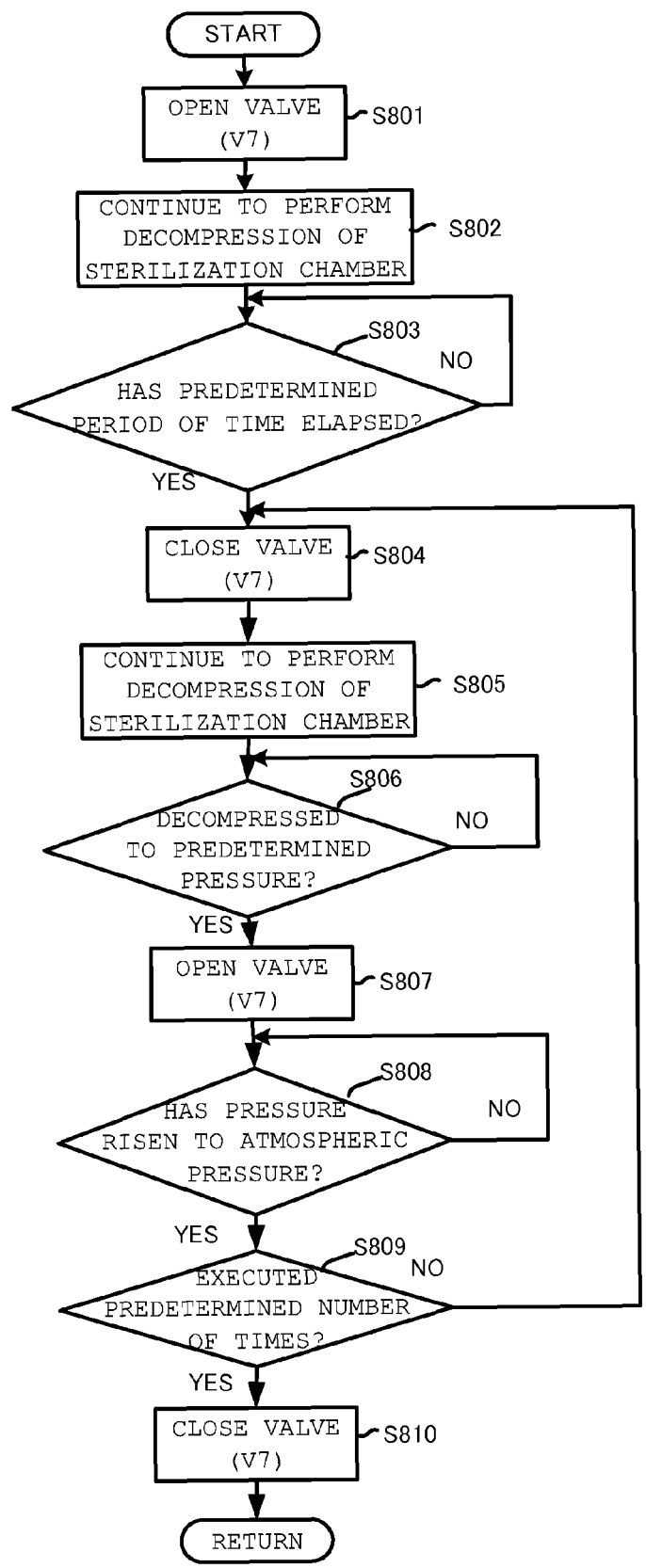
FIG. 8 is a diagram illustrating an example of detailed processing of the ventilation step illustrated in step S503 of FIG. 5.

FIG. 8 is a flowchart illustrating an example of detailed processing of the exhaust step illustrated in step S503 of FIG. 5. Each step (process) illustrated in FIG. 8 is performed by the operation of each apparatus within the sterilization apparatus being controlled by the computation processing unit 201 of the sterilization apparatus 100. That is, each step (process) illustrated in the drawing is executed by controlling the operation of each apparatus by executing a computer-readable program and by the computation processing unit 201 of the sterilization apparatus 100.

Further, in step S801, the sterilization apparatus 100 opens the valve (V7) 226. Furthermore, in step S802, the sterilization apparatus 100 continues to perform suctioning (vacuuming) in the sterilization chamber 219 using the air transfer vacuum pump 220.

After opening the valve (V7) 226 in step S801, suctioning (vacuuming) is performed in the sterilization chamber 219 using the air transfer vacuum pump 220 in step S802, and after a predetermined period of time has elapsed (YES in step S803), the valve (V7) 226 is closed in step S804, and the air transfer vacuum pump 220 continues performing suctioning (vacuuming) in the sterilization chamber 219. Thereby, the pressure is reduced in the sterilization chamber 219.

Further, when the pressure in the sterilization chamber 219 is reduced to a predetermined pressure (50 Pa) (YES in step S806), the sterilization apparatus 100 opens the valve (V7) 226 in step S807. Thereby, external air outside the sterilization apparatus 100 that has been cleaned using the intake HEPA filter 210 is drawn into the sterilization chamber 219. Because pressure in the sterilization chamber 219 is lower than pressure outside the sterilization apparatus 100, external air outside of the sterilization apparatus 100 is drawn into the sterilization chamber 219.

Next, the sterilization apparatus 100 determines whether the pressure in the sterilization chamber 219 is raised up to the atmospheric pressure, and in a case where the pressure in the sterilization chamber 219 is raised up to the atmospheric pressure (YES in step S808), determines if the processing from steps S804 to S808 has been performed a predetermined number of times (for example, 4 times) in step S809. In a case where the process from steps S804 to S808 has been performed the predetermined number of times (for example, 4 times) (YES in step S809), the sterilization apparatus 100 closes the valve (V7) 226 in step S810, and terminate the exhaust step.

On the other hand, in a case where the processing from steps S804 to S808 has not been performed a predetermined number of times (for example, 4 times) (NO in step S809), the processing is repeated from step S804.

Thereby, the sterilizing agent that has adhered to the inner surfaces of the sterilization chamber 219 and sterilizing agent remaining as gas in the sterilization chamber 219 are suctioned by the air transfer vacuum pump 220. Here, the suctioned gas (including the sterilizing agent) passes through the exhaust HEPA filter 221, the sterilizing agent is decomposed in the sterilizing agent decomposition apparatus 222 and the molecules are discharged to the outside after decomposition.

Figure 9:
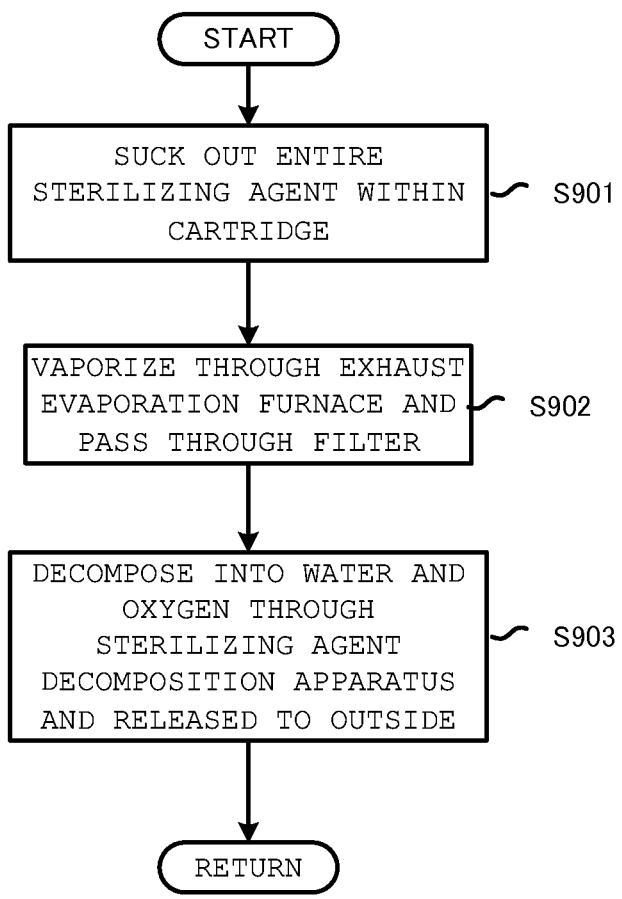
FIG. 9 is a diagram illustrating an example of detailed processing of the sterilizing agent discharge process illustrated in step S114 of FIG. 4B.

Next, referring to FIG. 9, an example of the sterilization discharge process illustrated in step S114 of FIG. 4B will be described in detail. FIG. 9 is a flowchart illustrating an example of the sterilization discharge process illustrated in step S114 of FIG. 4B in detail.

Each step illustrated in FIG. 9 is performed by the operation of each apparatus within the sterilization apparatus being controlled by the computation processing unit 201 of the sterilization apparatus 100. That is, each step illustrated in FIG. 9 is executed by controlling the operation of each apparatus by executing a computer-readable program by the computation processing unit 201 of the sterilization apparatus 100.

First, in step S901, the sterilization apparatus 100, using the rotary liquid transfer pump 223, suctions all the liquid sterilizing agent in the cartridge 205 using the pump, and the entire sterilizing agent which is sent through the conduit pipe between the liquid sensor 204 and the rotary liquid transfer pump 223 is sent into the exhaust evaporation furnace 224 through the conduit pipe between the rotary liquid transfer pump 223 and the exhaust evaporation furnace 224.

Next, in step S902, the sterilization apparatus 100, using the exhaust evaporation furnace 224, heats the entire liquid sterilizing agent (sterilizing agent which is accumulated in the exhaust evaporation furnace 224) which is transferred through the conduit pipe between the rotary liquid transfer pump 223 and the exhaust evaporation furnace 224, using a heater provided in the exhaust evaporation furnace 224, and the entire sterilizing agent is vaporized. Next, the vaporized sterilizing agent is transferred to the exhaust HEPA filter 221 through the conduit pipe between the exhaust evaporation furnace 224 and the exhaust HEPA filter 221.

Here, the heater provided in the exhaust evaporation furnace 224 is heated to a temperature higher than the boiling point of the sterilizing agent (hydrogen peroxide), for example (the boiling point of hydrogen peroxide is 141° C.). Therefore, the entire sterilizing agent is vaporized by the exhaust evaporation furnace 224.

Further, using the exhaust HEPA filter 221, the sterilization apparatus 100 cleans the vaporized sterilizing agent transferred through the conduit pipe between exhaust evaporation furnace 224 and the exhaust HEPA filter 221, and the cleaned gas (including sterilizing agent) is transferred to the sterilizing agent decomposition apparatus 222 through the conduit pipe between the sterilizing agent decomposition apparatus 222 and the exhaust HEPA filter 221.

Further, in step S903, the sterilizing agent decomposition apparatus 222 decomposes the molecules of the sterilizing agent included in the gas that is transferred from the conduit pipe between the sterilizing agent decomposition apparatus 222 and the exhaust HEPA filter 221, and discharges the molecules generated by decomposition to the outside of the sterilization apparatus 100.

Further, referring to FIG. 10, a block configuration of a hardware configuration of concentration furnace 208, a valve (V1) 211, a valve (V3) 212, a valve (V4) 213, a measuring pipe 214, a valve (V2) 215, a vaporization furnace 216, a valve (V5) 217, and a valve (V9) 227 of the sterilization apparatus 100 according to the present invention will be described.

Figure 10:
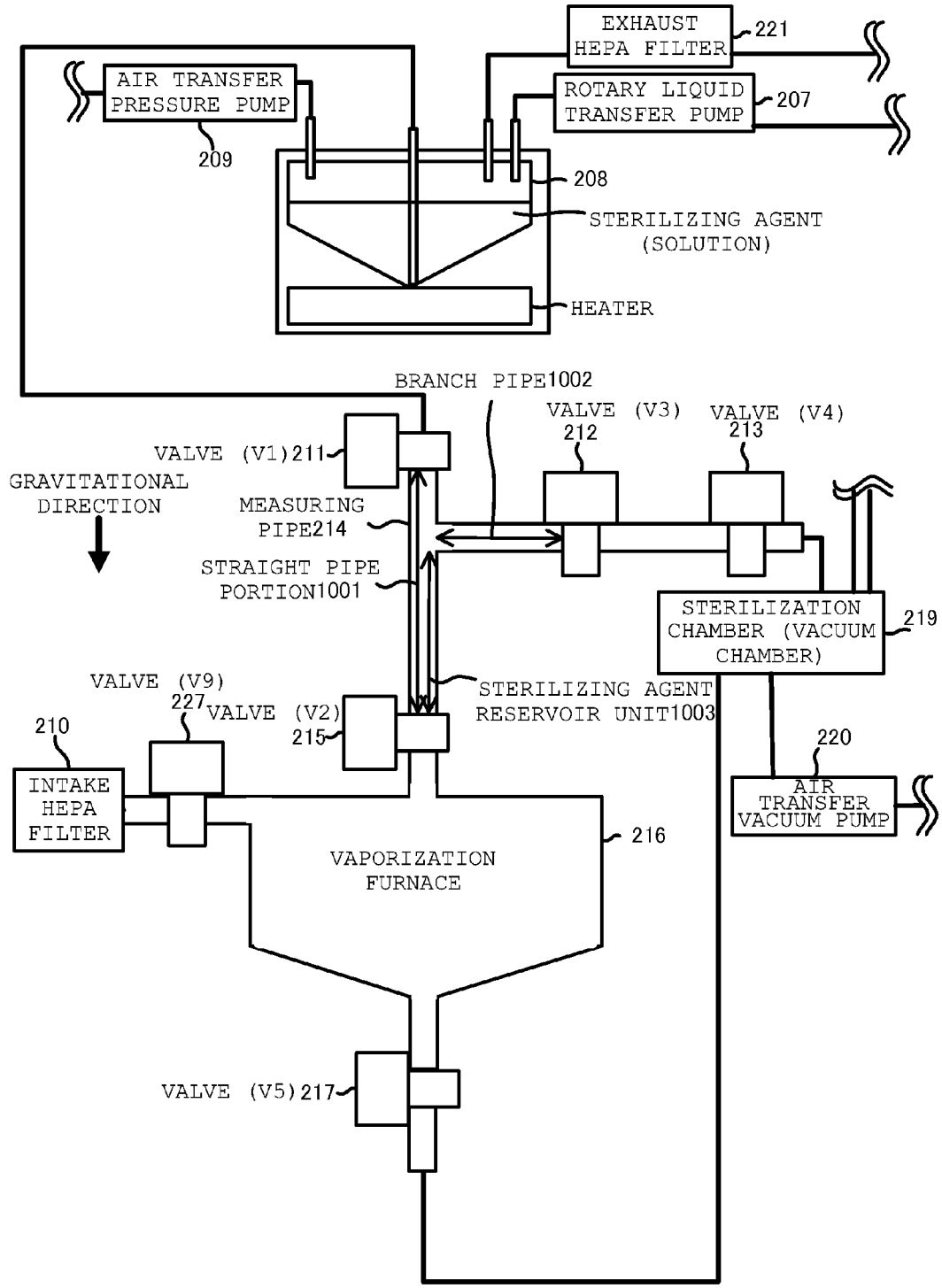
FIG. 10 is a block diagram illustrating an example of hardware configurations of a concentration furnace 208, a valve (V1) 211, a valve (V3) 212, a valve (V4) 213, a measuring pipe 214, a valve (V2) 215, a vaporization furnace 216, a valve (V5) 217, and a valve (V9) 227 of the sterilization apparatus 100 according to an embodiment of the present invention.

FIG. 10 is a diagram illustrating an example of the block configuration diagram of the hardware configuration of the concentration furnace 208, the valve (V1) 211, the valve (V3) 212, the valve (V4) 213, the measuring pipe 214, the valve (V2) 215, the vaporization furnace 216, the valve (V5) 217 and the valve (V9) 227 of the sterilization apparatus 100 according to the present invention.

In FIG. 10, the same hardware components as those illustrated in FIG. 2 are respectively denoted by the same reference numerals.

In steps S704 and S729, the rotary liquid transfer pump 207 is operated, a predetermined amount (for example, 2 ml) of the sterilizing agent within the cartridge 205 is sucked out, and the predetermined amount of sucked out sterilizing agent is placed in the concentration furnace 208.

In step S706, the concentration furnace 208, as illustrated in FIG. 10, is provided with a heater at the lower portion of the concentration furnace 208, and the sterilizing agent is heated by the heat of this heater. In a case where the sterilizing agent is aqueous solution of hydrogen peroxide, water is vaporized by the heat of the heater. Further, the vaporized water is forced into the conduit pipe that is conducted with the exhaust HEPA filter 221 by the air that is fed through the conduit pipe from the air transfer pressure pump 209, and is exhausted from the concentration furnace 208. In this way, the sterilizing agent (aqueous solution of hydrogen peroxide) is concentrated.

As described referring to FIG. 7B, in step S710, the sterilizing agent in the concentration furnace 208 enters into the measuring pipe 214. The measuring pipe 214, as illustrated in FIG. 10, includes a straight pipe portion 1001 and a branch pipe portion 1002. The straight pipe portion 1001 is a portion of the straight tube. The straight pipe portion 1001 is disposed vertically so that it is substantially in the gravitational direction.

In addition, the branch pipe portion 1002 is a tubular portion which extends like a branch from the intermediate or upper sections of the straight pipe portion 1001. The straight pipe portion 1001 is provided to be orthogonal to the axial center of the straight pipe portion and the axial center of the branch pipe portion 1002.

With such a configuration, the straight pipe portion 1001 in the measuring pipe 214 is configured so that the sterilizing agent entering from the concentration furnace 208 accumulates therein. The portion of the straight pipe portion 1001 where the sterilizing agent accumulates is called a sterilizing agent reservoir 1003. In other words, the sterilizing agent reservoir 1003 has a space sufficient to contain the sterilizing agent entering from the concentration furnace 208.

Therefore, the sterilizing agent entering from the concentration furnace 208 accumulates in the sterilizing agent reservoir 1003, and the air entering from the concentration furnace 208 with the sterilizing agent together is filled in the space other than the space of the sterilizing agent that accumulates in sterilizing agent reservoir 1003. That is, since the space other than the space of sterilizing agent is a space that communicates with the space in the branch pipe portion 1002 in the branch pipe portion 1002, in step S711, the air is sucked into the sterilization chamber 219 by opening the valve (V3) 212 and the valve (V4) 213.

Further, by opening the valve (V2) in step S714, the sterilizing agent that accumulates in sterilizing agent reservoir 1003 is drawn into the vaporization furnace 216 to vaporize. As illustrated in FIG. 10, the sterilizing agent is easily vaporized by the liquid sterilizing agent entering the vaporization furnace 216 from the upper portion of the vaporization furnace 216.

Further, as illustrated in FIG. 10, the conduit pipe between the intake HEPA filter 210 and the vaporization furnace 216 is provided on the upper portion of the vaporization furnace 216. Therefore, when the valve (V9) opens in step S719, because air flows out from the upper portion of the vaporization furnace 216 to the sterilization chamber 219 at the bottom of the vaporization furnace 216, the sterilizing agent attached to the inner side of the vaporization furnace 216 and the vaporized sterilizing agent in the vaporization furnace 216 can be easily removed from a wide area, and the removed sterilizing agent can be easily flown to the sterilization chamber 219.

Figure 12:
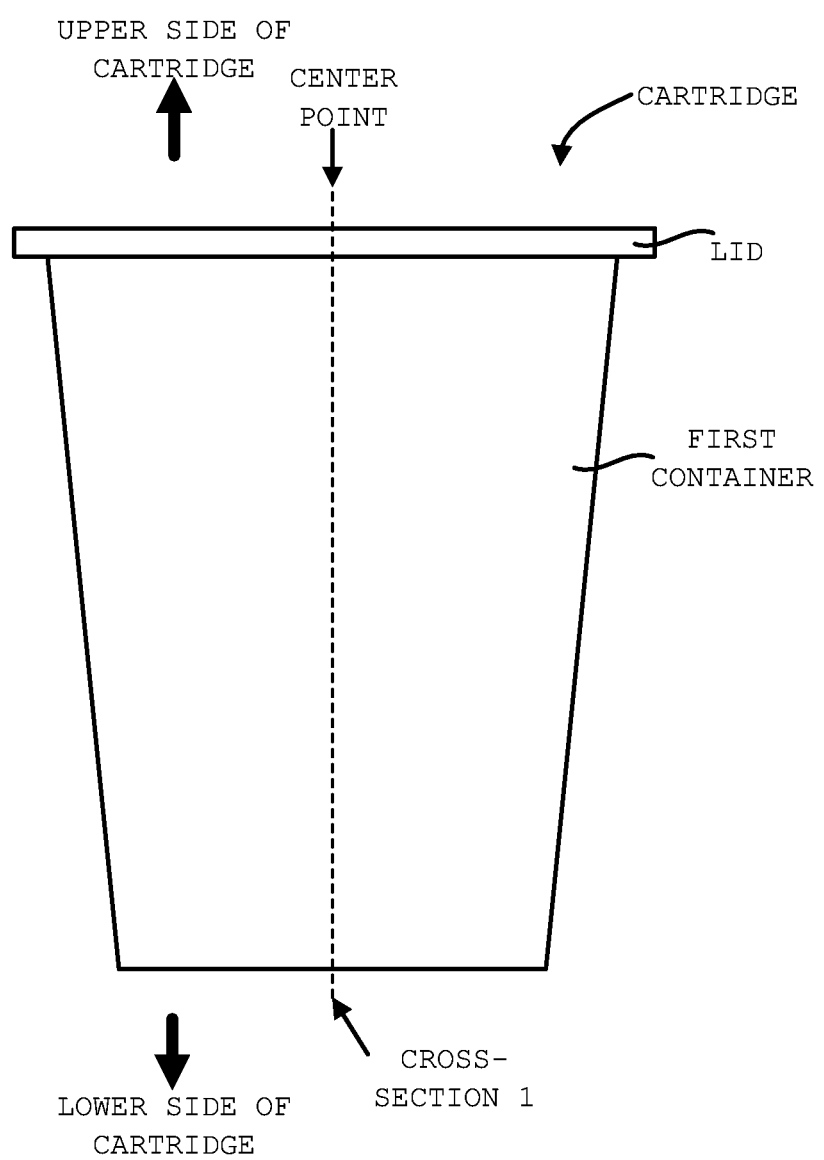
FIG. 12 is a diagram viewed from a side of a cartridge 205 of a sterilizing agent used in the sterilization apparatus according to an embodiment of the present invention.

Next, the cartridge 205 and a state in which a syringe needle is inserted into the cartridge 205 will be described referring to FIGS. 12 and 13. FIG. 12 is a diagram of the cartridge 205 of the sterilizing agent used in the sterilization apparatus viewed from the side.

The cartridge illustrated in FIG. 12 is a cartridge containing an amount of sterilizing agent to be able to perform a sterilization process a plurality of times in one bottle. A medicinal solution such as hydrogen peroxide used as the sterilizing agent is stored in the cartridge illustrated in FIG. 12.

As illustrated in FIG. 12, the cartridge is configured by a first container and a lid for the first container. The external appearance of the first container has a cup-like shape. Further, the material of the first container is polypropylene (plastic) which has resistance to hydrogen peroxide that is the sterilizing agent. The first container is also provided to protect a second container described below.

The lid is a lid for closing the first container onto the upper side of the first container. That is, the lid is adhered to the rim of the outer circumference of the first container. Further, the material of the lid is propylene (plastic) which has resistance against hydrogen peroxide that is a sterilizing agent. The cross-section of the cartridge at the center point of the cartridge seen from above is referred to as a cross-section 1.

Next, referring to FIG. 13, the configuration when an extraction needle (syringe needle) for sucking out the sterilizing agent within the cartridge is inserted into the cartridge according to the present invention will be described. FIG. 13 is a cross-sectional diagram of the cross-section 1 of the cartridge according to the present invention.

The extraction needle (syringe needle) is inserted into a hole in the lid, that is, a hole in the cap, by the sterilization apparatus 100 operating to lower the extraction needle (syringe needle) from above the cartridge toward the cartridge.

At this time, the sterilization apparatus 100 operates so that the distal end of the syringe needle reaches the lower end of a second container 409 by penetrating the hole in the lid, that is, the hole in the cap.

Figure 13:
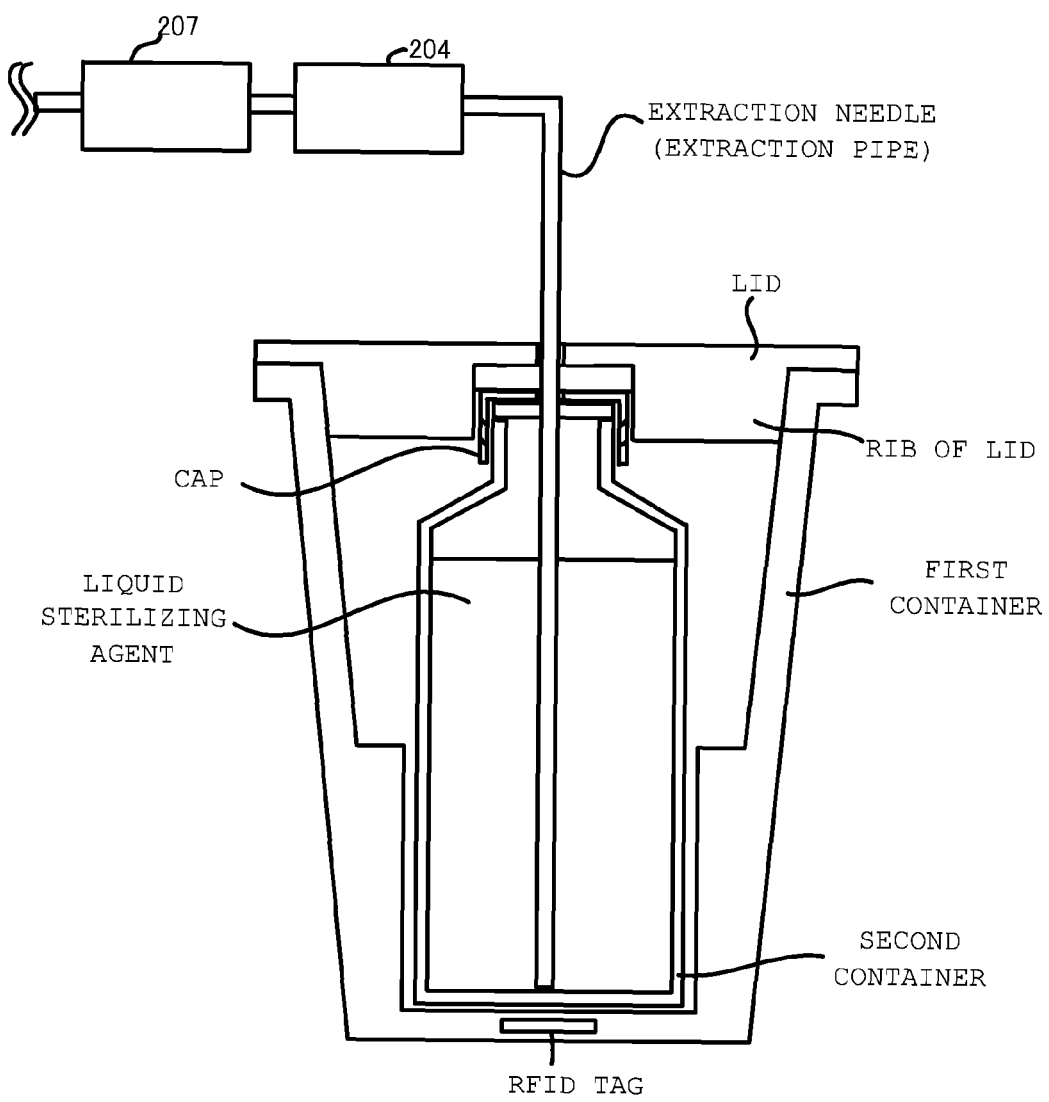
FIG. 13 is a cross-sectional diagram taken along a cross-section 1 of the cartridge according to an embodiment of the present invention.

As illustrated in FIG. 13, in step S103, by inserting a syringe needle in the cartridge, the sterilizing agent within the cartridge can be extracted and the cartridge is prevented from being taken out.

Figure 14:
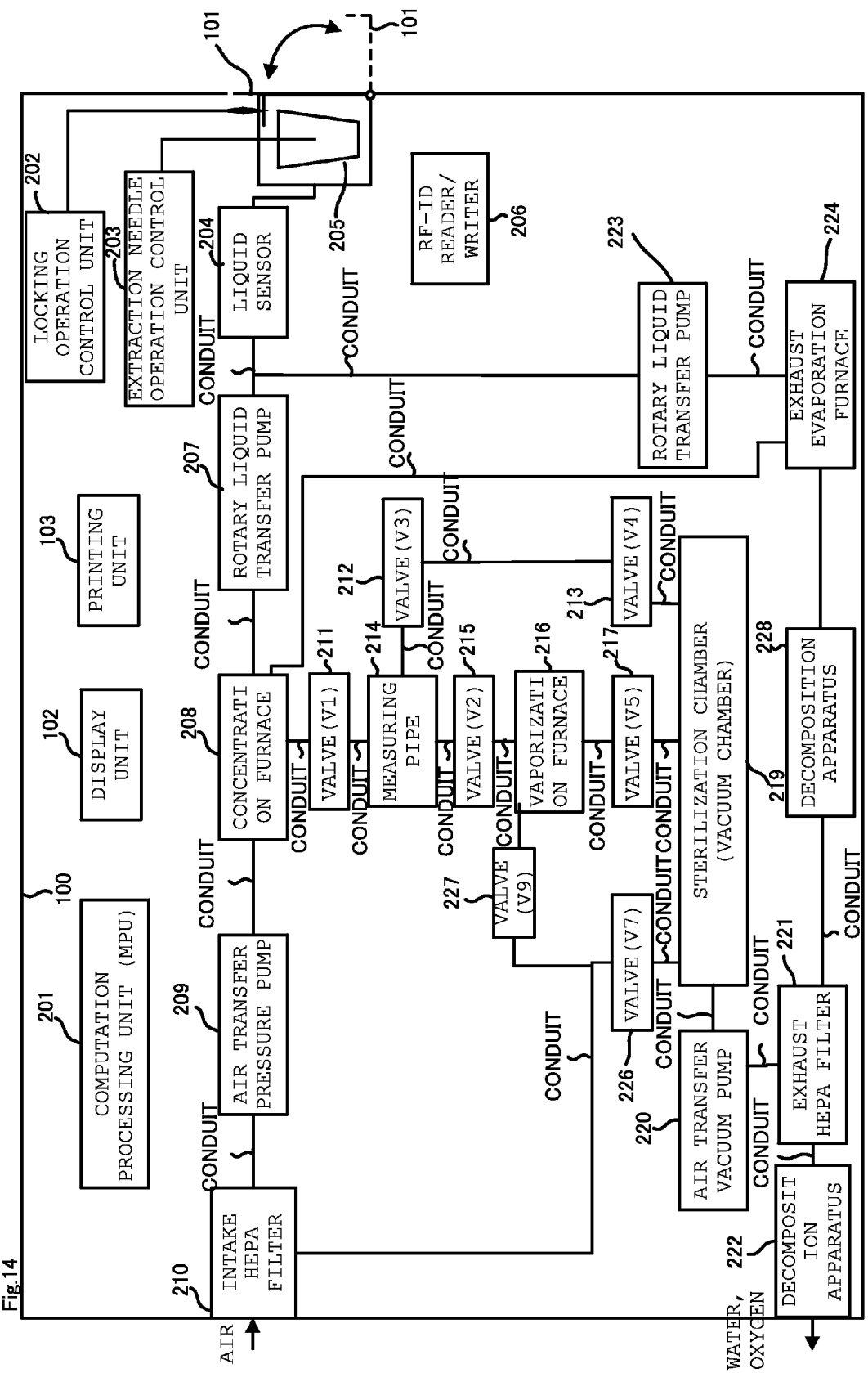
FIG. 14 is a diagram illustrating an example of a hardware configuration of the sterilization apparatus according to an embodiment of the present invention.

A sterilization apparatus according to a second embodiment of the present invention will be described below referring to FIG. 14. The second embodiment will be described mainly about portions that differ from the sterilization apparatus described in the first embodiment. FIG. 14 is a block diagram illustrating an example of the hardware configuration of the sterilization apparatus according to the present invention.

While a conduit pipe that can directly conduct the concentration furnace 208 with the exhaust HEPA filter 221 is provided on the sterilization apparatus 100 described in the first embodiment, in the second embodiment, a conduit pipe that can directly connect the concentration furnace 208 with the exhaust HEPA filter 221 is not provided. However, in the second embodiment, a conduit pipe that can conduct the concentration furnace 208 with the exhaust evaporation furnace 224 is provided, as illustrated in FIG. 14.

Further, while a conduit pipe that can directly conduct the exhaust evaporation furnace 224 with the exhaust HEPA filter 221 is provided on the sterilization apparatus 100 described in the first embodiment, it is not provided in the second embodiment. Instead, in the second embodiment a sterilizing agent decomposition apparatus 228 is additionally provided between the exhaust evaporation furnace 224 and the exhaust HEPA filter 221.

That is, in the sterilization apparatus 100 of the second embodiment, as illustrated in FIG. 14, the sterilizing agent decomposition apparatus 228 is provided between the exhaust evaporation furnace 224 and the exhaust HEPA filter 221. Further, a conduit pipe that can conduct the exhaust evaporation furnace 224 with the sterilizing agent decomposition apparatus 228 and a conduit pipe that can conduct the sterilizing agent decomposition apparatus 228 with the exhaust HEPA filter 221, are provided.

Other than the configurations described above, the sterilization apparatus 100 of the second embodiment is the same as the sterilization apparatus 100 of the first embodiment. That is, since the sterilization apparatus 100 of the second embodiment has the configuration illustrated in FIG. 14, the sterilization apparatus 100 of the second embodiment is controlled as follows.

The concentration furnace 208 concentrates the sterilizing agent by heating the sterilizing agent sent in from the rotary liquid transfer pump 207 through a conduit pipe using a heater, and evaporating (vaporizing) the moisture and the like included in the sterilizing agent. The vaporized water is discharged from the concentration furnace 208 by being pushed out from within the concentration furnace 208 into a conduit pipe conducted with the exhaust evaporation furnace 224 by the air send in from the air transfer pressure pump 209 through a conduit pipe.

Furthermore, the gas and/or liquid (the liquid is a liquid generated from the gas vaporized in the concentration furnace 208 being condensed within the conduit pipe directly conducting the concentration furnace 208 with the exhaust evaporation furnace 224) entering the exhaust evaporation furnace 224 from the concentration furnace 208 through a conduit pipe directly conducting the concentration furnace 208 with the exhaust evaporation furnace 224 is heated by the heater in the exhaust evaporation furnace 224 again, and the temperature of the gas is increased further. As a result, the gas is less likely to be condensed.

Further, the condensed liquid is vaporized by being heated again by the heater in the exhaust evaporation furnace 224. Furthermore, the heated gas and/or the vaporized gas is transferred to the sterilizing agent decomposition apparatus 228 from the exhaust evaporation furnace 224 through the conduit pipe directly conducting the exhaust evaporation furnace 224 with the sterilizing agent decomposition apparatus 228.

Further, similar to the sterilizing agent decomposition apparatus 222, a catalyst for decomposing the sterilizing agent is provided in the sterilizing agent decomposition apparatus 228. Therefore, when the vaporized sterilizing agent is transferred from the exhaust evaporation furnace 224 to the sterilizing agent decomposition apparatus 228, the catalyst and the sterilizing agent react, then the sterilizing agent is decomposed.

In a case where the sterilizing agent is hydrogen peroxide, for example, the catalyst for decomposing the sterilizing agent is, for example, manganese dioxide. In such a case, in the sterilizing agent decomposition apparatus 228, the hydrogen peroxide reacts with the manganese dioxide to be decomposed into water and hydrogen.

Since the reaction in which the hydrogen peroxide is decomposed into water and hydrogen is a heating reaction, that is, since the boiling points of water and hydrogen are lower than that of the hydrogen peroxide, the gas containing hydrogen peroxide is decomposed into water and hydrogen in the sterilizing agent decomposition apparatus 228, heated further, and converted into a gas of a state that is not easily condensed.

Furthermore, the gas containing the water (water vapor) and oxygen generated by the sterilizing agent decomposition apparatus 228 being decomposed passes through the conduit pipe connecting the sterilizing agent decomposition apparatus 228 with the exhaust HEPA filter 221, and is sent to the exhaust HEPA filter 221.

Here, since the gas transferred to the exhaust HEPA filter 221 (for example, water and oxygen) has a lower boiling point than the gas (for example, hydrogen peroxide) transferred from the exhaust evaporation furnace 224 to the sterilizing agent decomposition apparatus 228 and at a high temperature. Therefore, the gas is not easily condensed. Thus, the gas transferred to the exhaust HEPA filter 221 is in a state where it is not easily condensed at the exhaust HEPA filter 221. Therefore, the liquid that is liquefied does not easily adhere to the exhaust HEPA filter 221.

If the exhaust HEPA filter 221 absorbs liquid, there is a concern that there is an extreme decrease in air permeability, and the exhaust HEPA filter 221 does not function normally. That is, for example, in a case where the air transfer pressure pump 209 or the air transfer vacuum pump 220 is operated in a state in which liquid is absorbed by the exhaust HEPA filter 221, there is a concern that air may be blocked in the exhaust HEPA filter 221, and the exhaust HEPA filter does not function normally.

In order to solve such an issue, the sterilization apparatus 100 of the second embodiment additionally includes the sterilizing agent decomposition apparatus 228 between the exhaust evaporation furnace 224 and the exhaust HEPA filter 221. With this configuration, liquid that is liquefied does not easily adhere to the exhaust HEPA filter 221, and the exhaust HEPA filter can function normally.

Since the process of the second embodiment partially differs from that of the sterilizing agent discharge process (FIG. 9) described in the first embodiment, the differences will be described below referring to FIG. 9.

In step S901, the sterilization apparatus 100 sucks out the entire liquid sterilizing agent within the cartridge 205 using the rotary liquid transfer pump 223, and transfers the entire sterilizing agent transferred through a conduit pipe between the liquid sensor 204 and the rotary liquid transfer pump 223 into the exhaust evaporation furnace 224 through a conduit pipe between the rotary liquid transfer pump 223 and the exhaust evaporation furnace 224.

Using the evaporation furnace 224, the entire liquid sterilizing agent (sterilizing agent accumulated in the exhaust evaporation furnace 224) transferred through the conduit pipe between the rotary liquid transfer pump 223 and the exhaust evaporation furnace 224 is heated by a heater provided in the exhaust evaporation furnace 224, and the entire sterilizing agent is vaporized. Furthermore, the vaporized sterilizing agent is transferred to the sterilizing agent decomposition apparatus 228 through a conduit pipe between the sterilizing agent decomposition apparatus 228 and the exhaust evaporation furnace 224.

Here, the entire sterilizing agent is vaporized by the heater provided in the exhaust evaporation furnace 224.

Furthermore, in step S902, the sterilizing agent decomposition apparatus 228 decomposes the sterilizing agent molecules contained in the gas transferred from the conduit pipe between the sterilizing agent decomposition apparatus 228 and the exhaust evaporation furnace 224, and transfers the molecules generated through the decomposition to the exhaust HEPA filter 221.

Furthermore, the sterilization apparatus 100 cleans the vaporized sterilizing agent transferred from the exhaust HEPA filter 221 through a conduit pipe between the sterilizing agent decomposition apparatus 228 and the exhaust HEPA filter 221, and the cleaned gas (containing the sterilizing agent) is transferred to the sterilizing agent decomposition apparatus 222 through a conduit pipe between the sterilizing agent decomposition apparatus 222 and the exhaust HEPA filter 221.

Furthermore, in step S903, the sterilizing agent decomposition apparatus 222 decomposes the sterilizing agent molecules contained in the gas transferred from the conduit pipe between the sterilizing agent decomposition apparatus 222 and the exhaust HEPA filter 221, and discharges the molecules generated through the decomposition to the outside of the sterilization apparatus 100.

In the first embodiment (for example, in a case where the user mistakenly cuts the main power while the hydrogen peroxide solution remaining in the cartridge 205 set in the sterilization apparatus 100 is subjected to evaporation decomposition process) since the operation of the air transfer pressure pump 209 is stopped, the flow of air is stopped, and the hydrogen peroxide steam vaporized in the exhaust evaporation furnace 224 is accumulated in the conduit pipe between the exhaust evaporation furnace 224 and the exhaust HEPA filter 221, the exhaust HEPA filter 221, and the conduit pipe between the exhaust HEPA filter 221 and the sterilizing agent decomposition apparatus 222.

As a result, there is a concern that the hydrogen peroxide steam accumulated in the conduit pipe between the exhaust evaporation furnace 224 and the exhaust HEPA filter 221, the exhaust HEPA filter 221, and the conduit pipe between the exhaust HEPA filter 221 and the sterilizing agent decomposition apparatus 222 is cooled by the surrounding temperature and is condensed.

Therefore, there may be an extreme decrease in air permeability if the exhaust HEPA filter 221 contains moisture, and the exhaust HEPA filter 221 is prone to be breaking easily. In a case where the air transfer vacuum pump 220 and the air transfer pressure pump 209 are operated in such a state, there is a concern that the air is blocked in the exhaust HEPA filter 221, and in the worst case, the exhaust HEPA filter 221 is unable to bear the pressure and may break.

Such an issue of the first embodiment can be resolved by the second embodiment.

More specifically, by providing the sterilizing agent decomposition apparatus 228 between the exhaust HEPA filter 221 and the exhaust evaporation furnace 224 and decomposing, using the sterilizing agent decomposition apparatus 228, the sterilizing agent transferred to the exhaust evaporation furnace 224 from the concentration furnace 208, and the sterilizing agent transferred to the exhaust evaporation furnace 224 by sucking out the sterilizing agent remaining in the cartridge 205, the sterilizing agent is not easily liquefied at the exhaust HEPA filter 221, and the product life of the exhaust HEPA filter 221 and the product life of the sterilization apparatus 100 can be extended.

Figure 15:
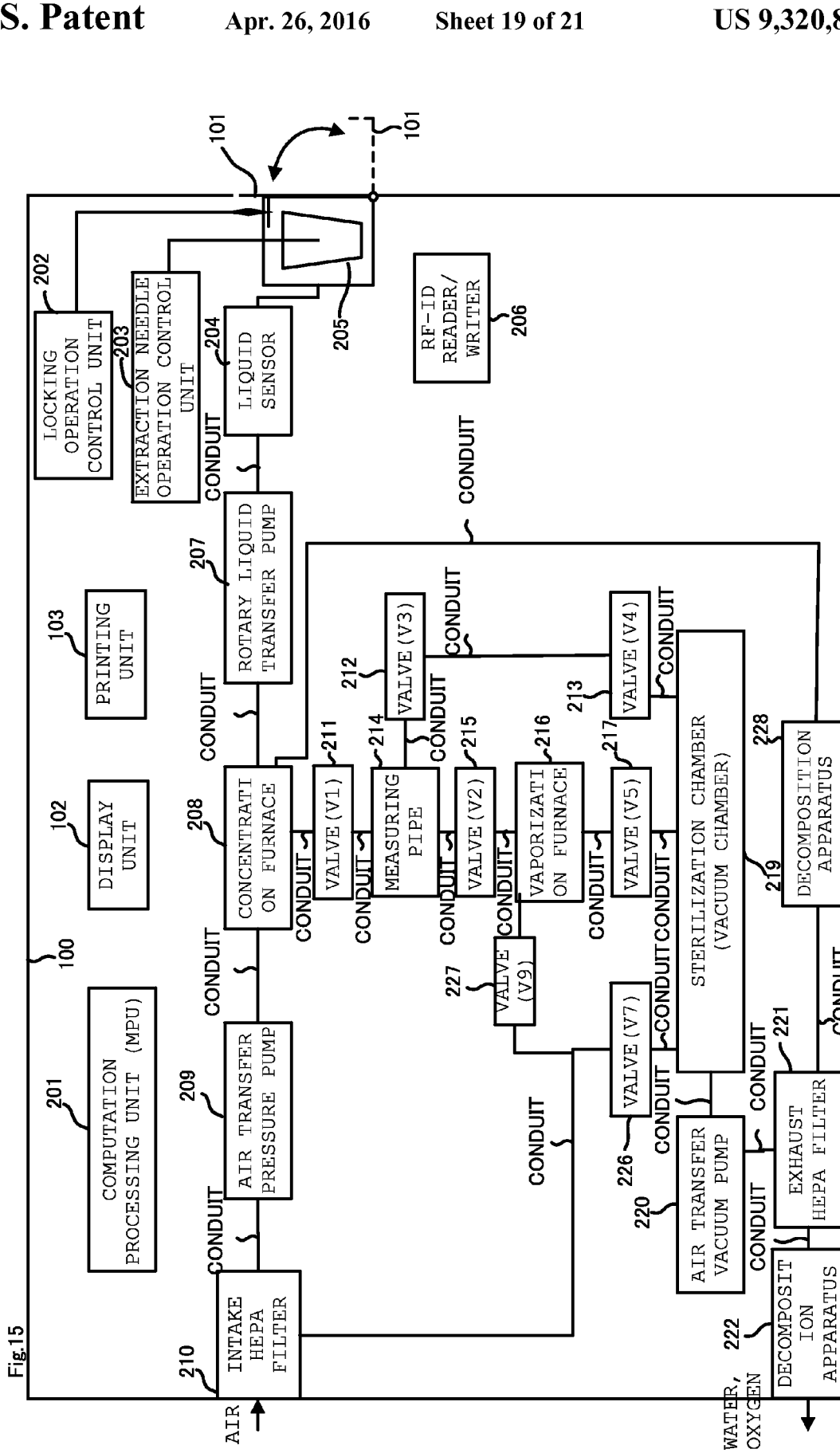
FIG. 15 is a diagram illustrating another example of a hardware configuration of the sterilization apparatus according to an embodiment of the present invention.

A sterilization apparatus according to a third embodiment of the present invention will be described below referring to FIG. 15. The third embodiment will be described mainly about portions that differ from the sterilization apparatus described in the first embodiment. FIG. 15 is a diagram illustrating an example of a hardware configuration of the sterilization apparatus according to the third embodiment.

While the conduit pipe that can directly conduct the liquid sensor 204 with the rotary liquid transfer pump 223, the rotary liquid transfer pump 223, the conduit pipe that can directly conduct the rotary liquid transfer pump 223 with the exhaust evaporation furnace 224, the exhaust evaporation furnace 224, and the conduit pipe that can directly conduct the exhaust evaporation furnace 224 with the exhaust HEPA filter 221, are provided in the sterilization apparatus 100 described according to the first embodiment, the above components are not provided in the sterilization apparatus 100 according to the third embodiment, as illustrated in FIG. 15.

Other than the configuration described above, the sterilization apparatus 100 of the third embodiment is the same as the sterilization apparatus 100 of the first embodiment. That is, the sterilization apparatus 100 of the third embodiment has the configuration illustrated in FIG. 15, and the sterilizing agent discharge processing in step S114 of FIG. 4B differs from that of the first embodiment.

Therefore, the sterilizing agent discharge process of step S114 of FIG. 4B will be described referring to FIG. 16 according to the third embodiment.

Figure 16:
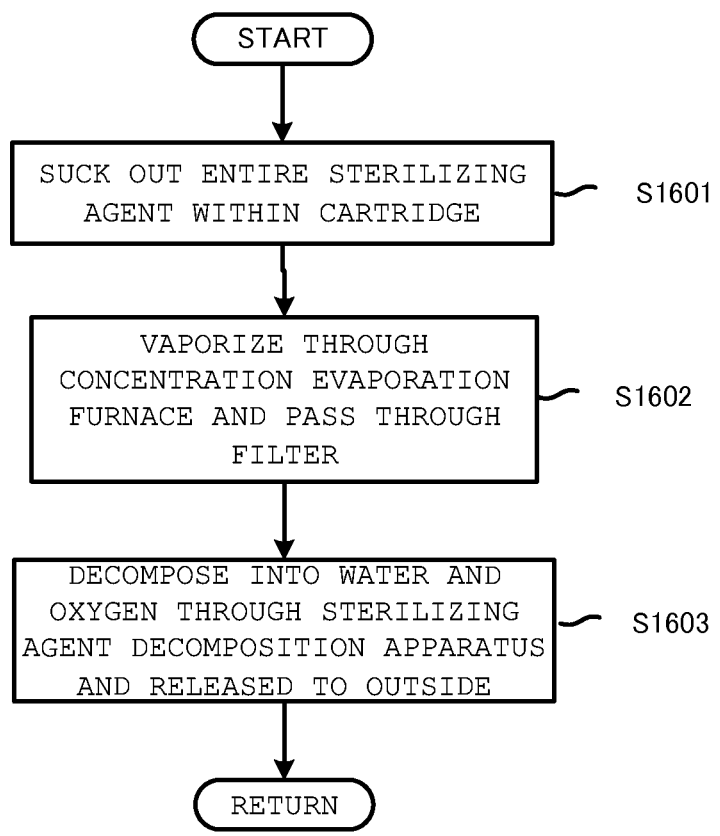
FIG. 16 is a diagram illustrating an example of detailed processing of the sterilizing agent discharge process illustrated in step S114 of FIG. 4B.

FIG. 16 is a flowchart illustrating an example of the detailed processing of the sterilizing agent discharge processing illustrated in step S114 of FIG. 4B. Each step illustrated in FIG. 16 is performed by the operation of each apparatus within the sterilization apparatus being controlled by the computation processing unit 201 of the sterilization apparatus 100.

When performing the step illustrated in FIG. 16, the valve (V1) 211 is closed. Even in a case where the valve (V1) 211 is opened, the step illustrated in FIG. 16 is performed after the valve (V1) 211 is closed.

First, in step S1601, the sterilization apparatus 100 sucks out the entire liquid sterilizing agent within the cartridge 205 using the rotary liquid transfer pump 207, and transfers the entire sterilizing agent transferred through a conduit pipe between the liquid sensor 204 and the rotary liquid transfer pump 207 to the concentration furnace 208 through a conduit pipe between the rotary liquid transfer pump 207 and the concentration furnace 208.

Furthermore, in step S1602, the sterilization apparatus 100 heats the entire liquid sterilizing agent (sterilizing agent accumulated in the concentration furnace 208) transferred from the concentration furnace 208 through the conduit pipe between the rotary liquid transfer pump 207 and the concentration furnace 208 using a heater provided in the concentration furnace 208, and vaporizes (also referred to as gasifying) the entire sterilizing agent. Furthermore, the vaporized sterilizing agent is transferred to the exhaust HEPA filter 221 through a conduit pipe between the exhaust HEPA filter 221 and the concentration furnace 208.

Here, the heater provided in the concentration furnace 208 is heated to a temperature (for example, 150° C.) higher than the boiling point (the boiling point of hydrogen peroxide is 141° C.) of the sterilizing agent (hydrogen peroxide). Therefore, the entire sterilizing agent is vaporized by the concentration furnace 208.

Furthermore, the sterilization apparatus 100 cleans the vaporized sterilizing agent transferred from the exhaust HEPA filter 221 through a conduit pipe between the concentration furnace 208 and the exhaust HEPA filter 221, and the cleaned gas (containing the sterilizing agent) is transferred to the sterilizing agent decomposition apparatus 222 through a conduit pipe between the sterilizing agent decomposition apparatus 222 and the exhaust HEPA filter 221.

Here, the hydrogen peroxide vaporized in the concentration furnace 208 is pushed out to the conduit pipe between the concentration furnace 208 and the exhaust HEPA filter 221 by the air transferred from the air transfer pressure pump 209 into the concentration furnace 208 through a conduit pipe between the air transfer pressure pump 209 and the concentration furnace 208, and is exhausted out of the concentration furnace 208.

Furthermore, in step S1603, the sterilizing agent decomposition apparatus 222 decomposes the sterilization molecules (hydrogen peroxide) contained in the gas transferred through the conduit pipe between the sterilizing agent decomposition apparatus 222 and the exhaust HEPA filter 221 using a catalyst (manganese dioxide), and discharges the molecules (water and oxygen) generated through decomposition to the outside of the sterilization apparatus 100.

In this way, unnecessary sterilizing agent (hydrogen peroxide or hydrogen peroxide water) within the cartridge 205 is decomposed, and the decomposed products (water and oxygen) are discharged to the outside.

In such a manner, since, according to the sterilizing agent discharge process of step S114 of FIG. 4B according to the third embodiment, the entire sterilizing agent extracted from the cartridge in which there is sterilizing agent remaining, heated, vaporized in the concentration furnace 208 is transferred to the exhaust HEPA filter through the conduit pipe directly connecting the concentration furnace 208 and the exhaust HEPA filter 221. Then, the sterilizing agent is further transferred from the exhaust HEPA filter 221 to the sterilizing agent decomposition apparatus 222 and is decomposed into water and oxygen. Therefore, the exhaust evaporation furnace 224 and the rotary liquid transfer pump 223 are not necessary, thereby allowing the sterilization apparatus 100 to be reduced in size and manufacturing cost.

A sterilization apparatus according to a fourth embodiment of the present invention will be described below referring to FIG. 17. The fourth embodiment will be described mainly with portions that differ from the sterilization apparatus described in the third embodiment. In the fourth embodiment, only the sterilizing agent discharge process of step S114 of FIG. 4B differs from that of the third embodiment.

Therefore, next, the sterilizing agent discharge process of step S114 of FIG. 4B according to the fourth embodiment will be described referring to FIG. 17. FIG. 17 is a flowchart illustrating an example of detailed processing of the sterilization discharge process illustrated in step S114 of FIG. 4B according to the fourth embodiment.

Figure 17:
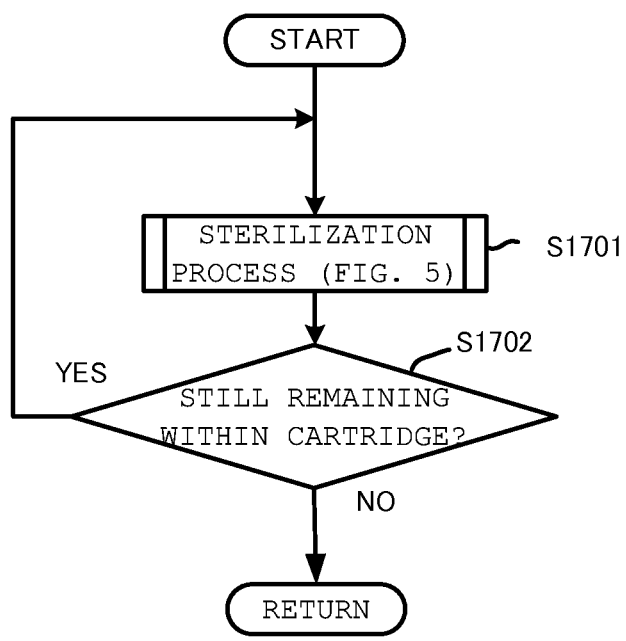
FIG. 17 is a diagram illustrating an example of detailed processing of the sterilizing agent discharge process illustrated in step S114 of FIG. 4B according to a fourth embodiment.

Each step (process) illustrated in FIG. 17 is performed by the operation of each apparatus within the sterilization apparatus being controlled by the computation processing unit 201 of the sterilization apparatus 100.

First, in step S1701, the sterilization apparatus 100 executes the sterilization process described above. The details of the sterilization process executed in step S901 is the process already described in FIG. 5.

That is, as a process for disposing of the sterilizing agent within the cartridge 205 (hydrogen peroxide or a hydrogen peroxide solution), the sterilization process (FIG. 5) is performed again.

Since the details of each of steps S501, S502, and S503 described in FIG. 5 have already been described, out of the details of the sterilization process performed in step S901, the steps that differ from the sterilization process performed in step S111 will be described, and description will be omitted where the processes are the same.

Figure 7A:
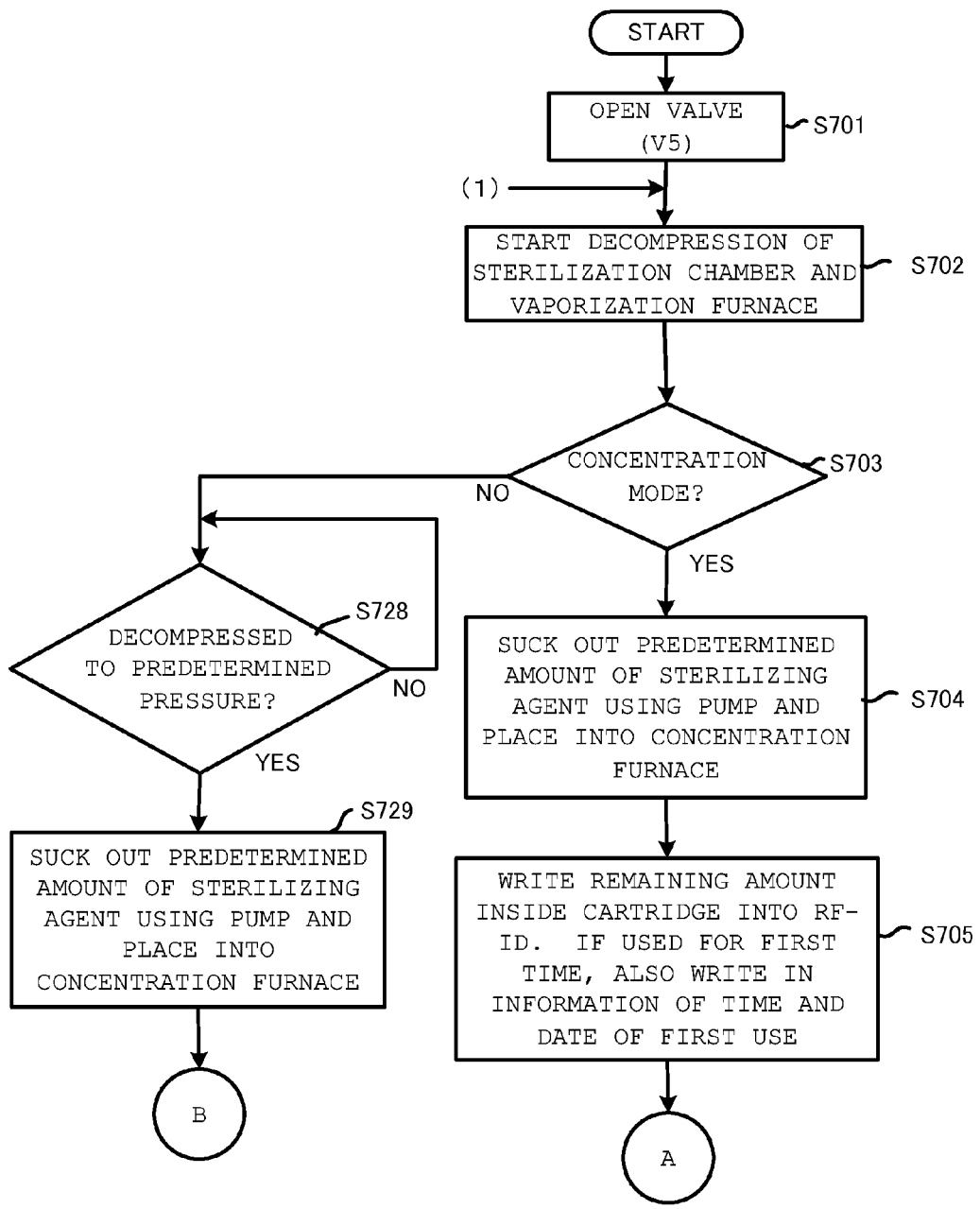
Figure 7C:
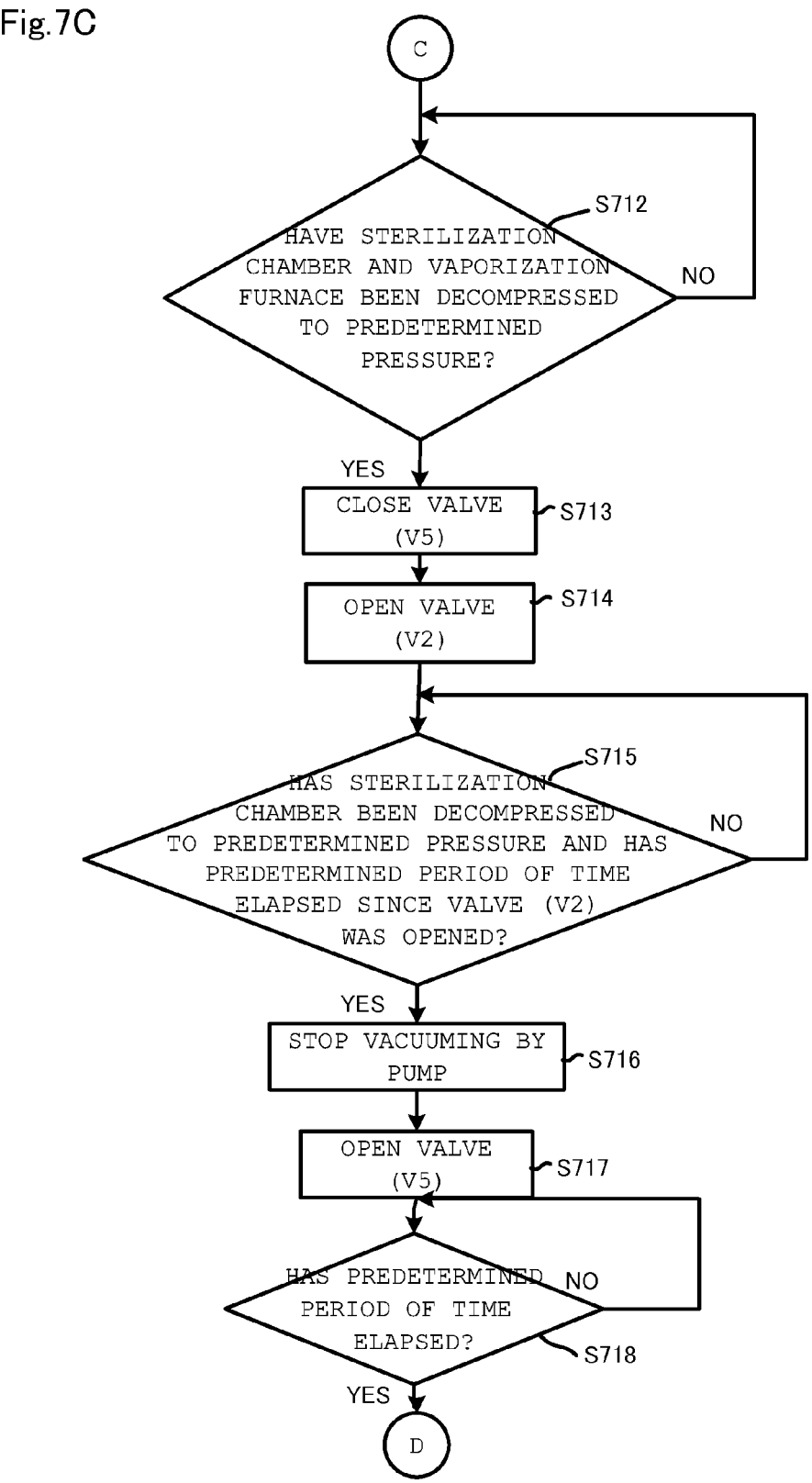
Figure 7D:
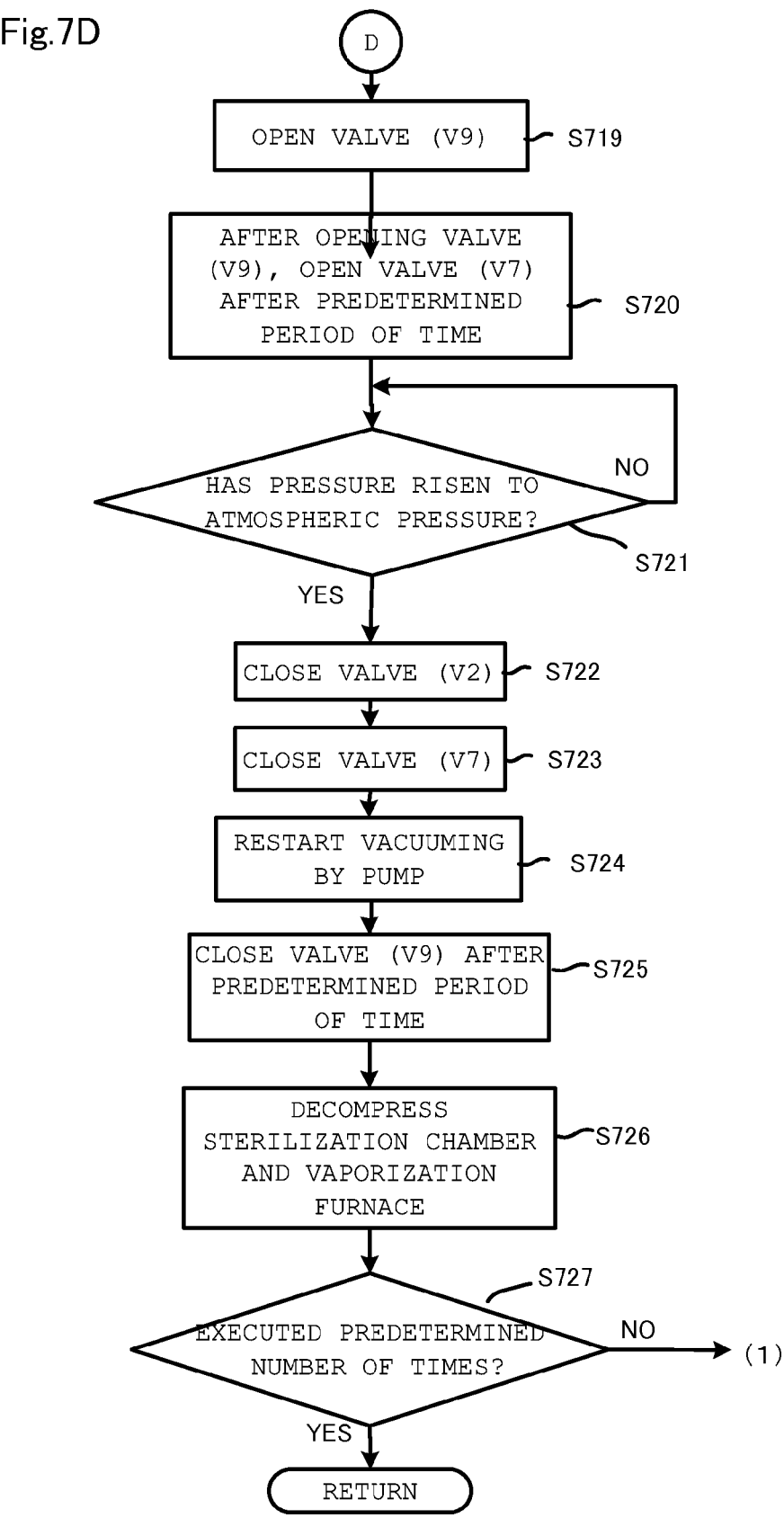

In step S703 of FIG. 7A, which is a detailed process step of the sterilization process of step S502, while it is determined in the sterilization process performed in step S111 whether a "sterilization mode through concentrating sterilizing agent" button 304 or "sterilization mode without concentrating sterilizing agent" button 305 is pressed. In the sterilization process performed in step S1701, one of the modes is set by the user in advance, and the processing according to the set mode is performed.

By performing the sterilizing agent discharge process in step S114 in this manner, the sterilizing agent (hydrogen peroxide or a hydrogen peroxide solution) within the cartridge 205 is vaporized, and the vaporized sterilizing agent is decomposed by the sterilizing agent decomposition apparatus 222 to generate water and oxygen, and is discharged outside.

That is, the sterilizing agent decomposition apparatus 222 decomposes the sterilizing agent molecules contained in the gas transferred through a conduit pipe between the sterilizing agent decomposition apparatus 222 and the exhaust HEPA filter 221, and discharges the molecules (water and oxygen) generated through decomposition to the outside of the sterilization apparatus 100.

Next, in step S1702, after performing the process of step S1701, the sterilization apparatus 100 determines whether there is sterilizing agent remaining within the cartridge 205. Then, in a case where there is sterilizing agent remaining within the cartridge 205 (YES in step S1702), the sterilization process of step S1701 is performed again, and in a case where there is no sterilizing agent remaining within the cartridge 205 (NO in step S1702), the sterilizing agent discharge process in step S114 is ended, and the processing proceeds to step S115.

Specifically, the determination process performed in step S1702 determines whether there is sterilizing agent remaining within the cartridge 205 from the remaining amount of the sterilizing agent within the cartridge 205 written into the RF-ID in step S705 or S730. That is, in a case where the remaining amount of the sterilizing agent within the cartridge 205 written into the RF-ID in step S705 or S730 indicates 0 (zero), it is determined that there is no sterilizing agent remaining within the cartridge 205 (NO in step S1702), and in a case where the remaining amount of the sterilizing agent within the cartridge 205 written into the RF-ID in step S705 or S730 indicates a positive value (YES in step S1702), it is determined that there is sterilizing agent remaining within the cartridge 205.

As described above, according to the fourth embodiment, in order that the user is unable to touch the sterilizing agent, a cartridge with sterilizing agent remaining therein is made to be unable to be taken out of the sterilization apparatus, and the disposal cost of the sterilizing agent can be reduced. Furthermore, according to the present embodiment, there is no need to additionally provide an apparatus that vaporizes the sterilizing agent to dispose of the sterilizing agent or a conduit pipe for conducting the vaporized sterilizing agent to be disposed of with a sterilizing agent decomposition apparatus, and costs necessary for the production of the sterilization apparatus can be reduced.

As described above, according to aspects of the present invention, a cartridge with sterilizing agent remaining therein can be prevented from being taken out from the sterilization apparatus so that the user does not touch the sterilizing agent.

While the present invention has been described with reference to embodiments, it is to be understood that the invention is not limited to the described embodiments.

The following numbered statements form part of the description. The claims follow these statements and are labeled as such.

Statement 1. A sterilization apparatus (100) for sterilizing an object by extracting a sterilizing agent from a cartridge (205) containing the sterilizing agent, the apparatus comprising:

reading means (206) for reading data from a storage medium of the cartridge, the data being used to determine whether to perform a process to dispose the sterilizing agent contained within the cartridge or not;

determining means (s104, S105, S106, S113) for determining whether performing the process to dispose the sterilizing agent or not, based on the data read by said reading means; and disposal means (S114) for executing the process to dispose the sterilizing agent, in a case where said determining means determines to perform the process to dispose the sterilizing agent.

Statement 2. The sterilization apparatus according to statement 1, further comprising:

extracting means for extracting the sterilizing agent from the cartridge; and updating means for updating the data stored the storage medium in response to extracting the sterilizing agent by said extracting means, wherein said determining means determines to perform the process to dispose the sterilizing agent or not using the data updated by said updating means.

Statement 3. The sterilization apparatus according to statement 1 or 2, Further comprising:
locking means (202 203) for locking a cartridge containing sterilizing agent and mounted on the sterilization apparatus;
releasing means (202 203) for releasing a lock by the locking means;
extracting means (207) for extracting the sterilizing agent from the cartridge; and
wherein the locking means is locked the cartridge without releasing by releasing means, until the sterilizing agent is extracted from the cartridge by extracting means.

Statement 4. A sterilization apparatus (100) for sterilizing an object by extracting a sterilizing agent from a cartridge in a sterilization process, the sterilization apparatus comprising:
extracting means for extracting a predetermined amount of the sterilizing agent from the cartridge, the predetermined amount of the sterilizing agent being used by the sterilization process;
wherein the extracting means performs to extract the sterilizing agent remaining within the cartridge after the predetermined amount of the sterilizing agent has extracted from the cartridge.

This application claims priority from Japanese Patent Applications No. 2011-222385 filed Oct. 6, 2011; No. 2011-239563 filed Oct. 31, 2011; No. 2011-239564 filed Oct. 31, 2011; and No. 2012-155735 filed Jul. 11, 2012 which are hereby incorporated by reference herein in their entirety.

What is claimed is:

1. A sterilization apparatus for sterilizing an object by extracting a sterilizing agent from a cartridge containing the sterilizing agent, the apparatus comprising:
a locking unit configured to lock the cartridge mounted on the sterilization apparatus and containing the sterilizing agent;
an extracting unit configured to extract the sterilizing agent from the cartridge,
a controlling unit configured to control the locking unit and the extracting unit; and
a sterilization chamber configured to store the object therein and sterilize the object using the sterilizing agent extracted by the extracting unit in a sterilization process,
wherein the controlling unit is configured to control the locking unit to lock the cartridge mounted on the sterilization apparatus, control the extracting unit to perform a first process of extracting a predetermined amount of sterilizing agent used in the sterilization process of sterilizing the object from the cartridge locked by the locking unit, control to perform the sterilization process for sterilizing the object using the predetermined amount of the sterilizing agent, and further perform a second process of extracting, from the locked cartridge from which the predetermined amount of sterilizing agent has been extracted, remaining sterilizing agent, of which an amount being not larger than the predetermined amount, that remains in the cartridge, and control the locking unit to release the lock of the cartridge after the extracting unit has completed the process of extracting the remaining sterilizing agent that remains within the cartridge without performing the sterilization process of sterilizing the object using the remaining sterilization agent extracted in the second process.

2. The sterilization apparatus according to claim 1, further comprising:
a disposal unit configured to dispose of sterilizing agent within the cartridge; and
wherein the controlling unit is configured to control the locking unit to release the lock of the cartridge after the disposal unit has disposed of the remaining sterilizing agent extracted by the extracting unit in the process of extracting the remaining sterilizing agent remaining in the cartridge locked by the locking unit.

3. The sterilization apparatus according to claim 2, wherein the disposal unit is arranged to dispose of the sterilizing agent within the cartridge by decomposing the sterilizing agent using a catalyst.

4. The sterilization apparatus according to claim 1,
wherein the cartridge comprises a storage medium for storing data relating to the sterilizing agent within the cartridge, and
wherein the sterilization apparatus further comprises a reading unit configured to read the data from the storage medium of the cartridge, and
wherein the controlling unit is configured to control the locking unit to lock the cartridge in a case where the data has been read, by the reading unit, from the storage medium of the cartridge mounted on the sterilization apparatus.

5. The sterilization apparatus according to claim 4 further comprising:
a determination unit configured to determine whether the data read by the reading unit satisfies a predetermined condition, and
wherein the controlling unit is configured to control the extracting unit to perform the process of extracting, from the cartridge locked by the locking unit, the remaining sterilizing agent remaining within the cartridge in a case where it is determined by the determination unit that the data read by the reading unit satisfies the predetermined condition.

6. The sterilization apparatus according to claim 5, wherein the data includes an amount of the sterilizing agent remaining within the cartridge, and
wherein the predetermined condition includes a condition of whether the amount of sterilizing agent remaining within the cartridge that is included in the data read by the reading unit is smaller than the amount of the sterilizing agent used in the sterilization process.

7. The sterilization apparatus according to claim 5, wherein the data read by the reading unit includes a date of manufacture of the cartridge, and
wherein the predetermined condition includes a condition of whether a predetermined time has elapsed from the date of manufacture of the cartridge read by the reading unit.

8. The sterilization apparatus according to claim 5, wherein the data read by the reading unit includes a date of first use of the cartridge, and
wherein the predetermined condition includes a condition of whether a predetermined time has elapsed from the date of first use of the cartridge read by the reading unit.

9. The sterilization apparatus according to claim 5, further comprising:
an updating unit configured to update the data stored the storage medium in response to the extracting unit extracting the sterilizing agent, wherein the determining unit is configured to determine whether the data as updated by the updating unit has fulfilled the predetermined condition.

10. The sterilization apparatus according to claim 9, wherein the updating unit is configured to, in a case where information of first use date of the cartridge cannot be read by the reading unit from the storage medium included in the cartridge, store in the storage medium information indicating a current date as a first use date of the cartridge.

11. The sterilization apparatus according to claim 9, wherein the data stored in the storage medium includes data relating to the amount of sterilizing agent remaining in the cartridge and the updating unit is configured to update the amount of sterilizing agent remaining in the cartridge that is included in the data stored in the storage medium based on an amount of the sterilizing agent extracted from the cartridge by the extracting unit.

12. The sterilization apparatus according to claim 5, wherein the data stored in the storage medium of the cartridge includes identification information of the cartridge, and the sterilization apparatus further comprises:

a storage unit configured to store identification information of the cartridge included in data read by the reading unit in a case where a disposal process to dispose the sterilizing agent contained within the cartridge has been performed; and wherein the determination unit is configured to determine whether to perform the disposal process of the sterilizing agent remaining within the cartridge or not, based on whether or not the identification information of the cartridge is stored in the storage unit.

13. The sterilization apparatus according to claim 1, wherein the sterilizing agent comprises a hydrogen peroxide solution.

* * * * *